(12) United States Patent
Ferri

(10) Patent No.: US 9,949,858 B2
(45) Date of Patent: Apr. 24, 2018

(54) FOOT-THERAPY AND TOE-ALIGNING DEVICE

(71) Applicant: FenF, LLC, Dexter, MI (US)

(72) Inventor: Frederic Ferri, Dexter, MI (US)

(73) Assignee: FENF, LLC, Dexter, MI (US)

( * ) Notice: Subject to any disclaimer, the term of this patent is extended or adjusted under 35 U.S.C. 154(b) by 0 days.

(21) Appl. No.: 14/594,760

(22) Filed: Jan. 12, 2015

(65) Prior Publication Data
US 2015/0126338 A1    May 7, 2015

Related U.S. Application Data

(60) Continuation of application No. 13/196,785, filed on Aug. 2, 2011, now Pat. No. 8,932,186, which is a
(Continued)

(51) Int. Cl.
*A61F 5/01* (2006.01)
*A61H 1/02* (2006.01)
(Continued)

(52) U.S. Cl.
CPC ............... *A61F 5/019* (2013.01); *A61F 5/10* (2013.01); *A61H 1/0237* (2013.01);
(Continued)

(58) Field of Classification Search
CPC .......................... A61F 5/019; A61H 2001/027
(Continued)

(56) References Cited

U.S. PATENT DOCUMENTS 276,558 A    5/1883    Brown, Jr.
365,572 A    6/1887    Boomer
(Continued)

FOREIGN PATENT DOCUMENTS

DE    276558    7/1914
DE    1076504    4/1960
(Continued)

OTHER PUBLICATIONS

Notice of Allowance for U.S. Appl. No. 11/541,067.
(Continued)

*Primary Examiner* — Loan H Thanh
*Assistant Examiner* — Jennifer M Deichl
(74) *Attorney, Agent, or Firm* — Tope-McKay & Associates

(57) ABSTRACT

Described is an exercise tool. More particularly, it is a therapy and exercise tool specifically devised as a foot-therapy and toe-aligning device to align, separate, and stretch toes. The foot-therapy and toe-aligning device comprises a frame with a plurality of posts connected with the frame. The device is formed of an elastic material such that a user may place at least one of the plurality of posts between a user's toes and pull the post to stretch and elongate the post between the toes. Upon release, the elastic material of the post causes the post to attempt to return to its original shape, thereby causing it to expand out and conform its shape to fit snugly against the user's toes. Additionally, the elastic material allows the toe posts to be positioned and maintained at numerous locations between the user's toes for customizable positioning between the toes.

2 Claims, 21 Drawing Sheets

Related U.S. Application Data continuation of application No. 11/982,390, filed on Oct. 31, 2007, now Pat. No. 8,002,675, which is a continuation-in-part of application No. 11/541,067, filed on Sep. 28, 2006, now Pat. No. 7,322,915, which is a division of application No. 10/687,354, filed on Oct. 17, 2003, now Pat. No. 7,131,939.

(51) Int. Cl.

| | | |
|---|---|---|
| *A61N 2/00* | (2006.01) | |
| *A61N 5/06* | (2006.01) | |
| *A63B 21/00* | (2006.01) | |
| *A63B 23/00* | (2006.01) | |
| *A63B 23/10* | (2006.01) | |
| *A63B 24/00* | (2006.01) | |
| *A61F 5/10* | (2006.01) | |
| *G09F 21/02* | (2006.01) | |
| *A63B 21/02* | (2006.01) | |

(52) U.S. Cl.
CPC ....... *A61H 1/0266* (2013.01); *A63B 21/4033* (2015.10); *A63B 23/10* (2013.01); *A63B 24/00* (2013.01); *G09F 21/02* (2013.01); *A61H 2001/027* (2013.01); *A61H 2201/0103* (2013.01); *A61H 2201/025* (2013.01); *A61H 2201/0207* (2013.01); *A61H 2201/0214* (2013.01); *A61H 2201/0228* (2013.01); *A61H 2201/0242* (2013.01); *A61H 2201/0257* (2013.01); *A61H 2201/10* (2013.01); *A61H 2201/105* (2013.01); *A61H 2201/5007* (2013.01); *A61H 2201/5082* (2013.01); *A61H 2201/5084* (2013.01); *A61H 2201/5097* (2013.01); *A61N 2/00* (2013.01); *A61N 2005/0651* (2013.01); *A63B 21/02* (2013.01); *A63B 2023/006* (2013.01); *A63B 2208/05* (2013.01); *A63B 2209/08* (2013.01); *A63B 2209/10* (2013.01); *A63B 2225/50* (2013.01); *A63B 2225/62* (2013.01); *A63B 2225/64* (2013.01); *A63B 2225/66* (2013.01); *A63B 2230/50* (2013.01)

(58) Field of Classification Search
USPC .......... 482/47, 79–80, 148; 30/26; 15/167.3; 132/75.6; 601/27, 40; D21/685; D28/56–61
See application file for complete search history.

(56) References Cited

U.S. PATENT DOCUMENTS

| | | | |
|---|---|---|---|
| 445,921 A | 2/1891 | Burlingame | |
| 525,059 A | 8/1894 | Ray et al. | |
| 633,422 A | 8/1899 | Burns et al. | |
| 1,095,213 A | 5/1914 | Johnson | |
| 1,096,397 A | 6/1914 | Pacorella | |
| 1,103,465 A * | 7/1914 | Arrowsmith | A61F 5/019 |
| | | | 602/30 |
| 1,349,085 A | 8/1920 | Mouse | |
| 1,402,375 A | 1/1922 | Parisi | |
| 1,867,679 A | 7/1932 | Riehle et al. | |
| 1,930,413 A | 10/1933 | Bruell | |
| 2,095,664 A | 10/1937 | Grenfell | |
| 2,153,493 A | 4/1939 | Yakimchick | |
| 2,223,204 A | 11/1940 | Carmichael | |
| 2,266,859 A | 12/1941 | Grampp | |
| 2,286,089 A | 6/1942 | Harris | |
| 2,335,665 A | 11/1943 | Goldmerstein | |
| 2,471,997 A | 5/1949 | Baltor | |
| 2,575,867 A | 8/1949 | Ferri | |
| 2,506,308 A | 5/1950 | Maynier | |
| 2,517,232 A | 8/1950 | Patulski | |
| 2,531,851 A | 11/1950 | Kiwad | |
| 2,546,118 A | 3/1951 | Wright | |
| 2,575,868 A | 11/1951 | Ferri | |
| 2,595,640 A | 5/1952 | Christopoulos | |
| 2,640,482 A | 6/1953 | Kiwad | |
| 2,740,207 A | 4/1956 | Starensier | |
| 2,751,693 A | 6/1956 | Baker | |
| 2,808,662 A | 10/1957 | Webb | |
| 2,947,095 A | 8/1960 | Miyachi | |
| 2,949,112 A | 8/1960 | Murray | |
| 3,011,281 A | 12/1961 | King | |
| 3,049,120 A | 8/1962 | Marcus | |
| 3,088,458 A | 5/1963 | Stewart | |
| 3,099,884 A | 8/1963 | Kixmiller et al. | |
| 3,128,763 A | 4/1964 | Langenfeld et al. | |
| 3,275,002 A | 9/1966 | Scholl | |
| 3,299,893 A | 1/1967 | Collina | |
| 3,416,542 A | 12/1968 | Shook | |
| 3,429,309 A * | 2/1969 | Kurth | A61F 5/019 |
| | | | 602/30 |
| 3,581,740 A | 6/1971 | Sherbourne | |
| 3,623,481 A | 11/1971 | Curran | |
| 3,724,458 A | 4/1973 | Piper | |
| 3,967,390 A | 7/1976 | Anfruns | |
| 4,017,989 A | 4/1977 | Perez, Jr. et al. | |
| 4,207,880 A | 6/1980 | Zinkovich | |
| 4,211,246 A | 7/1980 | Hokama | |
| 4,263,902 A | 4/1981 | Dieterich | |
| D260,047 S | 8/1981 | Heinz | |
| 4,300,294 A | 11/1981 | Riecken | |
| D271,156 S | 11/1983 | Williamson | |
| 4,419,839 A | 12/1983 | Wong | |
| 4,821,481 A | 4/1989 | Rieffel | |
| D306,084 S | 2/1990 | Volz et al. | |
| 4,914,837 A | 4/1990 | Rieffel | |
| 4,936,300 A | 6/1990 | Funatogawa | |
| 5,003,997 A | 4/1991 | Stewart et al. | |
| 5,039,093 A | 8/1991 | Collier | |
| 5,062,625 A | 11/1991 | Vonk | |
| 5,076,263 A * | 12/1991 | Funatogawa | 602/30 |
| 5,087,036 A | 2/1992 | Cooper | |
| D325,968 S | 5/1992 | Nofsinger | |
| 5,136,911 A | 8/1992 | Wyss | |
| D335,299 S | 5/1993 | Guidry | |
| 5,327,918 A | 7/1994 | Stewart et al. | |
| 5,374,226 A | 12/1994 | Grahm | |
| 5,466,202 A | 11/1995 | Stern | |
| 5,523,734 A | 6/1996 | Beck et al. | |
| 5,702,354 A | 12/1997 | DeSpain | |
| 5,723,785 A | 3/1998 | Manning | |
| D393,931 S | 4/1998 | Rue | |
| 5,749,377 A | 5/1998 | Desario | |
| 5,813,078 A | 9/1998 | Hogan, Sr. | |
| 5,870,837 A | 2/1999 | Poulos | |
| 5,893,221 A | 4/1999 | Weissman et al. | |
| 5,946,823 A | 9/1999 | Yates | |
| D415,858 S | 10/1999 | Funatogawa | |
| D420,785 S | 2/2000 | Perez | |
| D428,673 S | 7/2000 | Ikeda | |
| 6,151,801 A | 11/2000 | Frederiksen et al. | |
| D439,704 S | 3/2001 | Ikeda | |
| 6,226,893 B1 | 5/2001 | Schlamp et al. | |
| 6,228,001 B1 * | 5/2001 | Johnson et al. | 482/48 |
| 6,238,357 B1 | 5/2001 | Kawaguchi et al. | |
| 6,298,580 B1 | 10/2001 | Tadayon | |
| 6,318,373 B1 | 11/2001 | Kasahara | |
| 6,352,096 B1 | 3/2002 | Walsh | |
| D459,547 S | 6/2002 | Wada et al. | |
| 6,481,443 B1 | 11/2002 | Moore-Johnson et al. | |
| D476,147 S | 6/2003 | Campbell | |
| 6,625,904 B1 | 9/2003 | Frederiksen et al. | |
| 6,629,943 B1 | 10/2003 | Schroder | |
| D481,828 S | 11/2003 | Goldberg et al. | |
| 6,678,971 B2 | 1/2004 | Brooks | |
| 6,719,714 B2 | 4/2004 | Sossong | |
| 6,748,604 B2 | 6/2004 | Duboff et al. | |
| 6,817,967 B1 | 11/2004 | Ott et al. | |
| 6,941,954 B1 | 9/2005 | Belcher | |

(56) References Cited

U.S. PATENT DOCUMENTS

| | | | |
|---|---|---|---|
| 7,121,019 | B2 | 10/2006 | Frederiksen et al. |
| 7,131,939 | B2 | 11/2006 | Ferri |
| D556,381 | S | 11/2007 | Kennedy |
| 7,322,915 | B2 | 1/2008 | Ferri |
| D600,818 | S | 9/2009 | Yang |
| 8,002,675 | B2 | 8/2011 | Ferri |
| 8,932,186 | B2 | 1/2015 | Ferri |
| 9,138,616 | B2 | 9/2015 | Ferri |
| 9,387,359 | B2 | 7/2016 | Ferri |
| 2002/0121030 | A1* | 9/2002 | Coleman ................. 36/11.5 |
| 2003/0029056 | A1 | 2/2003 | Frederiksen et al. |
| 2004/0055179 | A1 | 3/2004 | Wang |
| 2006/0243291 | A1 | 11/2006 | Daley |
| 2007/0027011 | A1 | 2/2007 | Ferri |
| 2009/0093345 | A1 | 4/2009 | Findeisen |

FOREIGN PATENT DOCUMENTS

| | | |
|---|---|---|
| DE | 1881215 | 10/1963 |
| DE | 3049528 | 7/1982 |
| DE | 3530511 | 3/1987 |
| DE | 29606182 | 9/1996 |
| DE | 10154185 | 5/2003 |
| FR | 1095213 | 5/1955 |
| GB | 155180 | 12/1920 |
| GB | 246375 | 1/1926 |
| GB | 365572 | 7/1930 |
| GB | 445921 | 4/1936 |
| GB | 525059 | 8/1940 |
| GB | 811791 | 4/1959 |
| GB | 2378891 | 2/2003 |
| JP | 1250257 | 10/1989 |
| WO | WO 9504512 | 2/1995 |
| WO | WO 0191674 | 12/2001 |

OTHER PUBLICATIONS

Issue Notification for U.S. Appl. No. 11/541,067.
"Yoga Toes," 1 page, http://www.yogapro.com, 2008.
"Ms. Pedicure Toe Separator," 1 page, http://store.facevaluesonline.com, 2008.
"Genki-kun One Step," 7 pages, http://www.dr-1.co.jp, 2008.
"Genki-kun Toe Stretcher," 12 pages, http://www.dr-1.co.jp, 2008.
"Toe Stretchers Strenghtening Premium Toe Trainers," 7 pages, http://www.healiohealth.com, 2008.
"Toe Flexers (C7315)," 1 page, http://www.harrietcarter.com, 2008.
"Genki-kun One-Step," 5 pages, http://www.dr-1.co.jp/e/onestep.html, 2008.
"Correct Toes," 3 pages, http://nwfootankle.com/home/toes, 2009.
Invalidity Contentions by Taylor Gifts regarding Claim 1 of U.S. Pat. No. 7,131,939 and Claim 33 of U.S. Pat. No. 7,322,915 in *FenF LLC* v. *Taylor Gifts, Inc.*, dated Oct. 17, 2011.
United States Court of Appeals for the Federal Circuit, *FenF, LLC*, Plaintiff-Appellee, v. *Smartthingz, Inc*, Defendant-Appellant, 2014-1490, Appeal from the United States District Court for the Eastern District of Michigan in No. 2:12-cv-14770-PJDMKM, Judge Patrick J. Duggan, Decided: Feb. 6, 2015.
Interlocutory Order regarding U.S. Pat. No. 8.002,675 in *FenF LLC* v. *Smartthingz, Inc.*, dated Jul. 25, 2013.
Office Action 1 for U S. Appl. No. 13/830,654, dated Aug. 20, 2013.
Response to Office Action 1 for U.S. Appl. No, 13/630,654, dated Nov. 20, 2013.
Office Action 2 for U.S Appl. No. 13/830,654, dated Feb. 24, 2014.
Issue Notification for U.S. Appl. No. 13/830,654, dated Sep. 2, 2015.
United States Court of Appeals for the Federal Circuit, *FenF, LLC*, Plaintiff-Appellee, v. *Smartthingz, Inc.*, Defendant-Appellant, 2014-1490, Appeal from the United States District Court for the Eastern District of Michigan in No. 2:12-cv-14770-PJDMKM, Judge Patrick J. Duggan, Decided Feb. 6, 2015.

Response to Office Action 1 (Election) for U.S. Appl. No. 13/196,785, dated Sep. 20, 2013.
Office Action 3 for U.S. Appl. No. 13/196,785, dated Jul. 29, 2014.
Response Office Action 3 for U.S. Appl. No. 13/196,785, dated Jul. 29, 2014.
Response to Office Action 1 for U.S. Appl. No. 11/982,390, dated Jul. 31, 2009.
Interview Summery for U.S. Appl. No. 11/982,390, dated Jan. 20, 2010.
Response to Interview Summary for U.S. Appl. No. 11/982,390, dated Jan. 26, 2010.
Office Action 1 for U.S. Appl. No. 11/541,067, dated Apr. 6, 2007.
Examiner's Amendment for U.S. Appl. No. 11/541,067, dated Dec. 17, 2007.
Notice of Allowance for U.S. Appl. No. 11/541,067, dated Jun. 28, 2007.
Office Action 1 for U.S. Appl. No. 11/982,390, dated Apr. 29, 2009.
Response to Office Action 1 for U.S. Appl. No. 11/982,390, dated May 29, 2009.
Office Action 2 for U.S. Appl. No. 11/982,390, dated Aug. 25, 2009.
Response to Office Action 2 for U.S. Appl. No. 11/982,390, dated Oct. 30, 2009.
USPTO Interview Summary for U.S. Appl. No. 11/982,390, dated Jan. 20, 2010.
Interview Summary for U.S. Appl. No. 11/982,390, dated Jan. 26, 2010.
Office Action 3 for U.S. Appl. No. 11/982,390, dated Mar. 31, 2011.
Notice of Allowance for U.S. Appl. No. 11/982,390, dated May 9, 2011.
United States Court of Appeals for the Federal Circuit, *FenF, LLC*, Plaintiff-Appellee, v. *Smartthingz, Inc.*, Defendant-Appellant, 2014-1490, Appeal from the United States District Court for the Eastern District of Michigan in No. 2:12-cv-14770-PJDMKM, Judge Patrick J. Duggan, Decided: Feb. 6, 2015.
Interlocutory Order regarding U.S. Pat. No. 8,002,675, in *FenF LLC* v. *Smarthingz, Inc.*, dated Jul. 25, 2013.
Office Action 1 for U.S. Appl. No. 13/830,654, dated Aug. 20, 2013.
Response to Office Action 1 for U.S. Appl. No. 13/830,654, dated Nov. 20, 2013.
Preliminary Amendment for U.S. Appl. No. 13/830,654, dated Nov. 20, 2013.
Office Action 2 for U.S. Appl. No. 13/830,654, dated Feb. 24, 2014.
Response to Office Action 2 for U.S. Appl. No. 13/830,654, dated Jul. 24, 2014.
Office Action 3 for U.S. Appl. No. 13/830,654, dated Sep. 24, 2014.
Response to Office Action 3 for U.S. Appl. No. 13/830,654, dated Feb. 24, 2015.
Office Action 4 for U.S. Appl. No. 13/830,654, dated Apr. 6, 2015.
Response to Office Action 4 for U.S. Appl. No. 13/830,654, dated Jun. 16, 2015.
Interview Summary U.S. Appl. No. 13/830,654, dated Feb. 2, 2015.
Interview Summary U.S. Appl. No. 13/830,654, dated Jun. 12, 2015.
Notice of Allowance for U.S. Appl. No. 13/830,654, dated Aug. 17, 2015.
Office Action 1 for U.S. Appl. No. 13/196,785, dated Jul. 30, 2013.
Election for U.S. Appl. No. 13/196,785, dated Sep. 16, 2013.
Second Preliminary Amendment for U.S. Appl. No. 13/196,785, dated Sep. 16, 2013.
Office Action 2 for U.S. Appl. No. 13/196,785, dated Oct. 10, 2013.
Interview Summary for U.S. Appl. No. 13/196,785, dated Oct. 6, 2014.
Interview Summary Response for U.S. Appl. No. 13/196,785, dated Oct. 13, 2014.
Notice of Allowance for U.S. Appl. No. 13/196,785, dated Dec. 5, 2014.
Office Action 1 for U.S. Appl. No. 14/858,828, dated Jan. 14, 2016.
Response to Office Action 1 for U.S. Appl. No. 14/858,828, dated Feb. 29, 2016.
Notice of Allowance for U.S. Appl. No. 14/858,828, dated Jun. 3, 2016.

(56) References Cited

OTHER PUBLICATIONS

Office Action 1 for U.S. Appl. No. 15/202,218, dated Nov. 18, 2016.

* cited by examiner

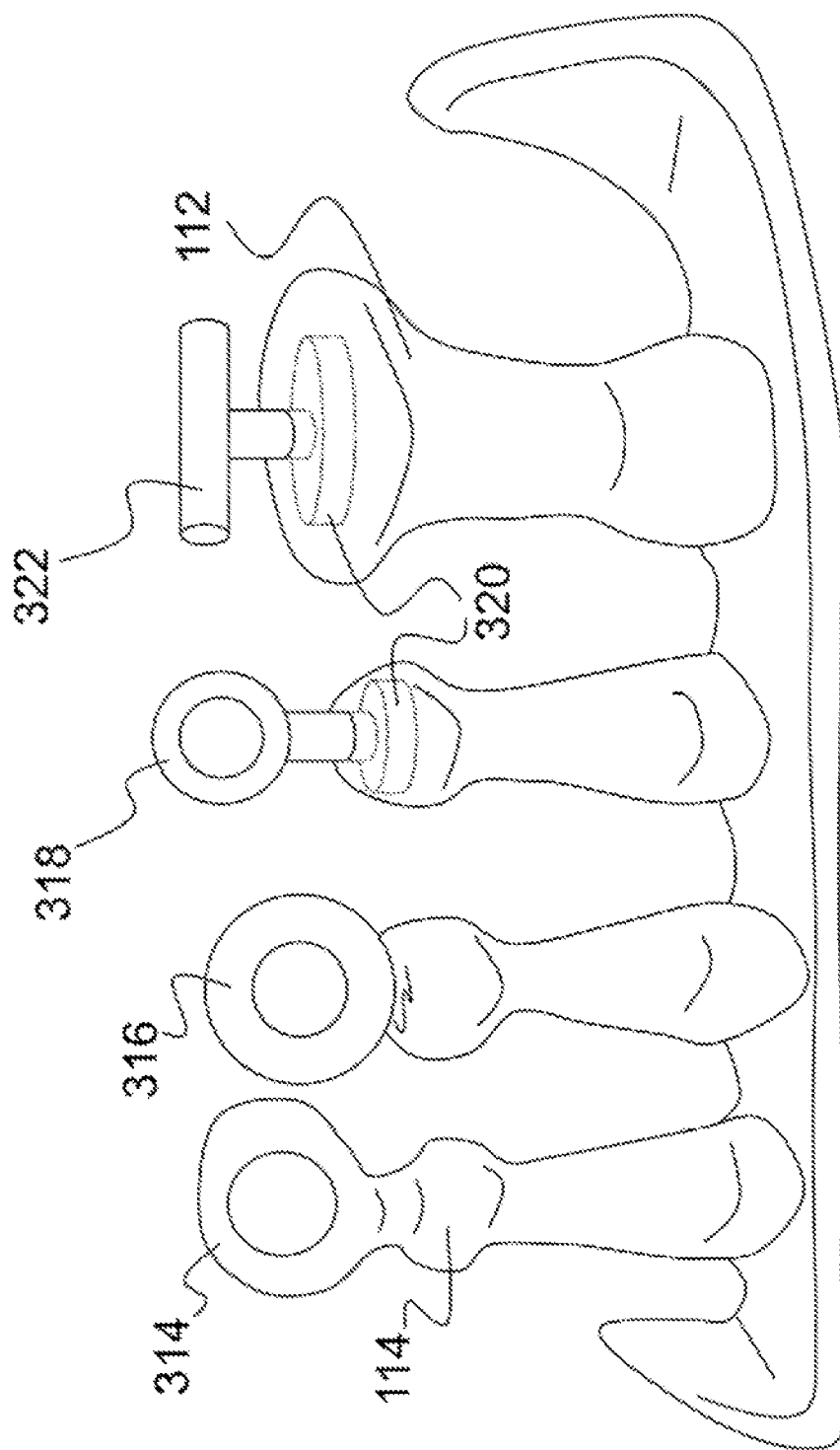

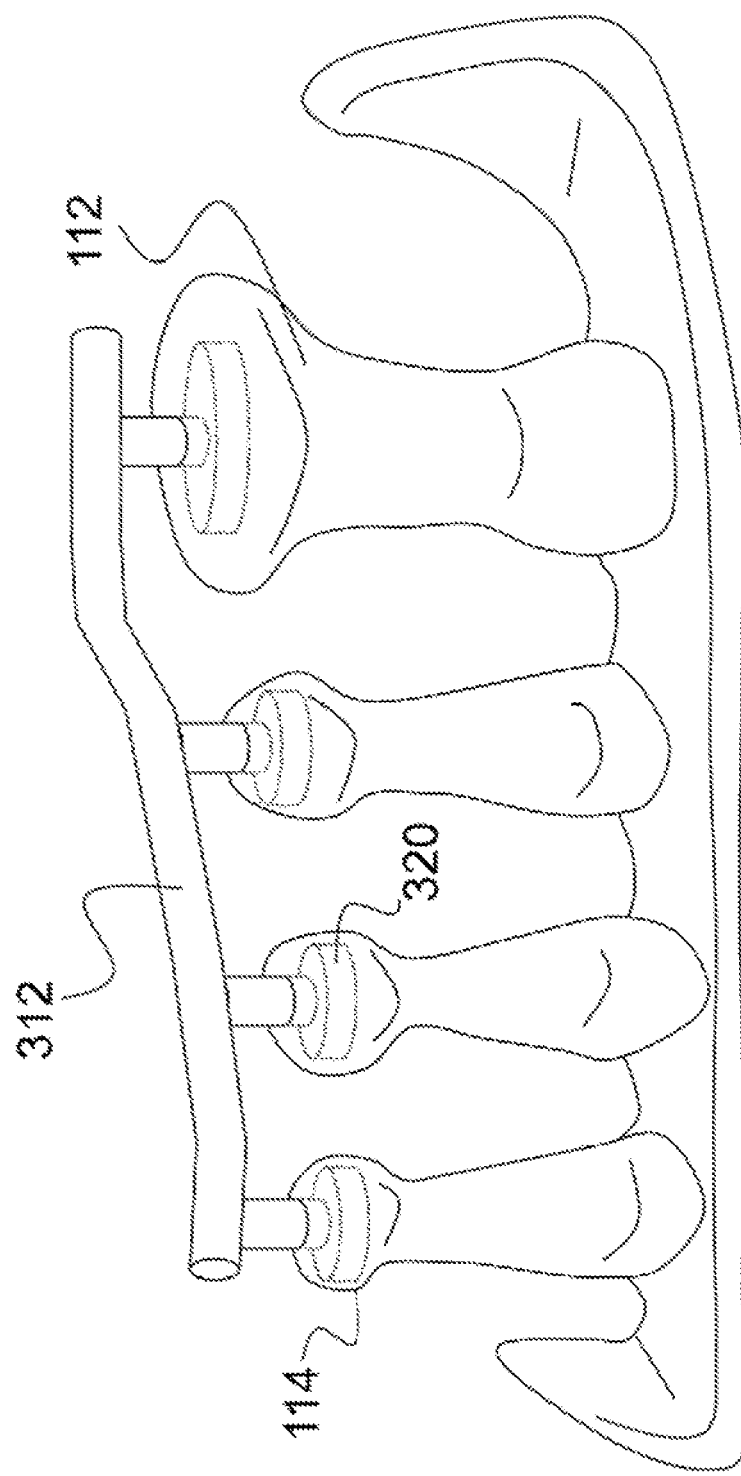

FOOT-THERAPY AND TOE-ALIGNING DEVICE

CROSS REFERENCE TO RELATED APPLICATIONS

This is a Continuation application of U.S. patent application Ser. No. 13/196,785, filed on Aug. 2, 2011, entitled, "Foot-Therapy and Toe-Aligning Device," which is a Continuation application of U.S. patent application Ser. No. 11/982,390, filed on Oct. 31, 2007, entitled, "Foot-Therapy and Toe-Aligning Device," now issued as U.S. Pat. No. 8,002,675, which is a Continuation-in-Part patent application of U.S. patent application Ser. No. 11/541,067, filed on Sep. 28, 2006, entitled, "Toe Stretcher," now issued as U.S. Pat. No. 7,322,915, which is a divisional application of U.S. application Ser. No. 10/687,354, filed on Oct. 17, 2003, entitled, "Toe Stretcher," now issued as U.S. Pat. No. 7,131,939.

BACKGROUND OF THE INVENTION (1) Field of the Invention

The present invention relates to an exercise tool, and more particularly, to a foot-therapy and toe-aligning device that is devised to align, separate, treat, and stretch toes.

(2) Description of Related Art

Therapy and exercise tools have long been known in prior art. Recently, such tools have been applied to not only stretch larger muscles, but also to those in the feet and toes. Several toe-stretching, exercising and aligning devices have been invented where a user places a toe stretcher (aligner) between the user's toes. However, as scientific understanding advances, more effective and convenient devices are now possible.

A few advantages of existing toe stretcher devices are that they generally increase foot strength, increase toe and ankle flexibility, improve arches, stretch Achilles' tendons, and realign toes. Although toe stretchers devised to-date partially fulfill this need, they are difficult to use and remain tied to past technology and information, limiting their convenience and effectiveness. By way of example, U.S. Pat. No. 5,076,263, issued to Funatogawa (hereinafter "the Funatogawa invention"), discloses a toe holder consisting of a frame with five holes (each separated by a toe post) for toe insertion. The five holes are substantially circular, with each circle being sealed around its perimeter. Because each circle is sealed, inserting all five toes has been problematic, making it difficult to put the toe stretcher on and take it off. Additionally, this design does not allow for the wide variations seen in foot/toe shape or condition. Thus, in some cases, the devices are unwearable. Additionally, altering the relative positioning of the individual posts to easily fit a specific person's foot, or condition is again impossible with the Funatogawa invention because the surrounding frame is connected with each toe post. This also makes it impossible to separate the frame for toe insertion. Separating the frame (i.e., pulling top and bottom portions of the frame away from each other) in the Funatogawa invention would pull the toe posts together, thereby causing the toe holes to become increasingly narrow upon elongation. Because the holes are sealed around their perimeter, the Funatogawa invention does not allow for a more custom, individual post positioning. Further, the Funatogawa invention does not mention a means to keep the post in a custom position (i.e., through elongation and return).

Additionally, the Applicant of the present invention previously filed U.S. patent application Ser. No. 10/687,354, entitled, "Toe Stretcher" (hereinafter "application '354), now issued as U.S. Pat. No. 7,131,939. Application '354 disclosed a toe stretcher having a frame with a separator for separating a plurality of toes. The frame included a top portion, a bottom portion, a front portion, and a back portion. The frame further included a plurality of holes through the frame for insertion of a plurality of toes, wherein each hole in the plurality of holes includes an entrance into the back portion, an exit from the front portion, and surrounding walls connecting the entrance with the exit. The surrounding wall in at least one hole in the plurality of holes is continuous and thereby sealed, and the surrounding wall in at least one other hole in the plurality of holes is non-continuous and thereby not sealed, serving as an openable toe hole allowing for easy insertion of a toe. While application '354 is particularly effective in stretching and aligning a user's toes, it requires a user to force at least one toe through a hole.

U.S. Pat. No. D415,858, issued to Funatogawa (hereinafter "the Funatogawa2 invention"), discloses a die-cut toe separator design, common in the cosmetic industry, having a bottom frame with at least four toe posts protruding up from the bottom frame. The toe separator in the Funatogawa2 invention appears to be formed of a die-cut foam and does not produce or teach a calculated balance of elastomeric properties and design shapes. Die-cut foam toe separators (for painting toe nails) are common and have been well known in the art for several years. Die-cut foam typically results in 90 degree angles, such as the 90 degree angles shown between the toe holes and the front and back portions (i.e., two-planes) of the frame in the Funatogawa2 invention. The two-plane, 90 degree cut and thickness represented in the Funatogawa2 invention would be extremely difficult if not impossible, to generate if the product disclosed in the Funatogawa2 invention was die-cut of an elastomeric gel material.

Additionally, the two-plane die-cutting design in the Funatogawa2 invention does not disclose ergonomically shaped toe posts. For beneficial effects, a user would ideally wear the product for an extended period of time, unlike cosmetic toe separators. Because of the sharp edges and two-plane thick posts, the Funatogawa2 invention disclosed in the design patent cannot be worn for extended periods as it would be extremely uncomfortable. The 90 degree edges and planer surfaces of the funtagowa2 invention would focus and localize pressure on the skin, the underlying muscle, the nerves, and the bone. As such, the Funatogawa2 invention was clearly not intended to be a therapeutic tool.

Due to the die-cut foam and its two-plane design, the toe separator disclosed in the Funatogawa2 invention could not have the required properties of elongation, contraction and compression resistance, and still be comfortable to use and impart therapeutic benefits.

Further, as noted in the illustrations of the Funatogawa2 invention, the proportionality of the thickness-to-length-to-height dimensions of the toe separator are sufficient to allow a user to place toes within the toe separator. However, the dimensions do not provide a sufficient proportionality to allow a user to stretch the toes outward and away from the ball of the foot. Thus, based on the illustrations of the Funatogawa2 invention, it is clear that the toe separator was designed as a cosmetic tool rather than an exercise and therapeutic device.

Additionally, foam does not elongate sufficiently to allow a user to stretch the toe post or frame. Thus, a need exists for an intended stretchable toe post (and/or frame) because in stretching, the toe post becomes thinner in diameter and is thereby more easily placed between the user's toes. Upon release, a stretched toe post would contract in length and expand circumferentially to conform tightly to and effectively hold the user's toes, thereby remaining in the desired position. When released, the post would expand outwardly to increase pressure against the toes and thereby hold the device in the desired position. Equally significant, the posts would contract along a lengthwise axis to impart a lengthwise axis compressive holding force on the surface of the toe as well, also holding the device in the desired position. The forces resulting from contraction and elongation, individually and in combination, would easily enable a user to place, affix and maintain a toe post position between a user's toes.

Therefore, it can be appreciated that a continuing need exists for a new and improved foot-therapy, exercise and aligning device that allows for axially, ergonomically-contoured post shapes, and a means of maintaining a post in a custom placed position through a calculated balance of elastomeric properties and design shape.

SUMMARY OF INVENTION

The present invention relates to an exercise tool, and more particularly, to an exercise tool devised as a foot-therapy device to align, separate, and stretch toes. In one aspect, the devices comprise a frame that includes a top portion and a bottom portion. A plurality of posts (that are formed of an elastic (e.g., elastomeric) material) are connected with and extend from the top portion of the frame, whereby a user may place at least one of the plurality of posts between a user's toes. The posts have a length, a diameter, and a circumference, and further possess elastic (e.g., elastomeric) properties.

In another aspect, each of the plurality of posts has an outer edge and further comprises a handle attached with the outer edge.

In yet another aspect, the handles include an attachment mechanism, allowing user to connect the handles using a connector that connects with the attachment mechanism.

In yet another aspect, the attachment mechanism includes holes formed through the plurality of handles such that a user can connect the handles by using a connector that passes through the holes.

Additionally, the elastic material is an elastomer gel.

In another aspect, the device (e.g., frame and/or posts) is formed of an elastic material, such as an elastomer gel.

In yet another aspect, the handle is formed as a ring to allow a user to grasp the ring and stretch a post.

Additionally, each of the plurality of posts has a length, an outer post surface, and a center post axis running the post length. Further, the elastic material in the post has a density, with the density varying from the outer post surface to the center post axis.

Furthermore, the frame has an outer frame surface, a frame length, and a center frame-axis running the frame length. Additionally, the elastic material in the frame has a density, with the density varying from the outer frame surface to the center frame-axis.

In yet another aspect, a rigid material is positioned within the frame for providing a rigid support.

In another aspect, an electronic device is attached with the foot-therapy and toe-aligning device. The electronic device is a device selected from a group consisting of a vibrating system for massaging and stimulating a user's toes, a light system, a heating system, a sensor, a cooling system, and a pulsating pressure mechanism.

In another aspect, a motion sensor is connected with an electronic device for actuating the electronic device.

In yet another aspect, a remote control is connected with the electronic device for allowing a user to selectively control the electronic device.

Additionally, the electronic device is controlled by a processing unit.

In another aspect, a controller chip is connected with the foot-therapy and toe-aligning device.

Further, the sensor is configured to provide feedback to a user when a predetermined threshold is reached. The feedback is provided in a manner selected from a group consisting of at least one of light, sound, vibration, and a change in temperature.

In yet another aspect, each of the plurality of posts has an exposed outer edge and further comprises a plurality of handles connected with the outer edge of each of the plurality of posts, where a handle is connected with an outer edge. Additionally, an electronic device is attached with the handle.

In another aspect, the frame has an outer frame surface, a frame length, and a center frame-axis running the frame length. Each of the plurality of posts has a length, an outer post surface, and a center post axis running the post length. A magnet is attached with the foot-therapy and toe-aligning device in a manner selected from a group consisting of being positioned within a post, being attached with the outer post surface of the post, being positioned within an interior of the frame, and being attached with the outer frame surface of the frame.

In another aspect, each of the plurality of posts has an exposed outer edge and further comprises a plurality of handles connected with the outer edge of each of the plurality of posts, where a handle is connected with an outer edge. Further, a magnet is attached with the handle.

In yet another aspect, a port is formed through at least one of the plurality of posts and/or frame. The port is formed to allow a user to insert a material into the port for dispersal proximate to a user's toes.

In another aspect, the frame has an outer frame surface and each of the plurality of posts has an outer post surface. Additionally, a reservoir is formed in at least one of the following: the outer post surface and the outer frame surface, whereby a user may position a material into the reservoir.

In yet another aspect, each of the plurality of posts has an exposed outer edge and further comprises a plurality of handles connected with the outer edge of each of the plurality of posts, where a single handle is connected with a single outer edge. Further, a reservoir is formed in the handle.

In another aspect, a footwear is attached with the frame.

In yet another aspect, the frame is formed as a shoe sole insert, thereby allowing a user to place the foot-therapy and toe-aligning device within a shoe and wear the shoe while treating the user's toes.

In another aspect, the present invention further comprises a shoe sole insert attached with the frame, thereby allowing a user to place the foot-therapy and toe-aligning device within a shoe and wear the shoe while treating the user's toes.

In another aspect, each handle is integrally formed with its corresponding post as a single piece.

In yet another aspect, the present invention further comprises a sleeve for positioning over a toe post.

In another aspect, a support structure is disposed within the toe post.

Further, the frame is formed of a transparent material, allowing light to pass through the material.

In yet another aspect, an implantation element is inserted within the frame.

In another aspect, the foot-therapy and toe-aligning device comprises an elongated post formed of an elastic material. The elongated post includes two opposing edges, whereby a user may use the two opposing edges to stretch the elongated post and place the now stretched elongated post between two adjacent toes, and where upon release, the elastic material of the post causes the post to conform its shape to fit snugly against the user's toes.

In yet another aspect, handles are attached at each of the two opposing edges, whereby a user may use the handles to stretch the elongated post. Additionally, the handles are integrally formed with the elongated post as a single piece.

In another aspect, the foot-therapy and toe-aligning device comprises a frame with a separator for separating a plurality of toes. The frame comprises a top portion, a bottom portion, a front portion, and a back portion. The frame further includes a plurality of holes through the frame for insertion of a plurality of toes. Each hole in the plurality of holes includes an entrance into the back portion, an exit from the front portion, and surrounding walls connecting the entrance with the exit. The surrounding walls in at least one hole in the plurality of holes is continuous and thereby sealed. Alternatively, the surrounding walls in at least one other hole in the plurality of holes is non-continuous and thereby not sealed, serving as an openable toe hole allowing for easy insertion of a toe, whereby a user may place the toe stretcher on the plurality of toes and effectively separate and stretch the toes.

In another aspect, the frame is formed of a transparent, elastic material and further includes an implantation element inserted within the frame.

In yet another aspect, a reservoir system is formed within the frame for receiving a material externally and applying the material to a user through use of the reservoir and the device.

In another aspect, an attachment mechanism is attached with the frame for allowing a user to attach an external object (such as an electronic device) with the device via the attachment mechanism. The electronic device can be attached internally or externally (using the attachment mechanism). Non-limiting examples of such an electronic device include a vibrator mechanism, a heating system, a cooling system, and a light system.

Finally, the present invention also includes a method for forming and using the device described herein. As can be appreciated by one skilled in the art, the method for forming the device comprises a plurality of acts of forming and attaching the device and related components. Further, the method for using the device comprises a plurality of acts applying and using the device as described below.

BRIEF DESCRIPTION OF THE DRAWINGS

The nature of the foot-therapy and toe-aligning device described herein will be readily apparent in the following drawings, in which:

FIG. 3B is a front-view of a foot-therapy and toe-aligning device, illustrating various handle configurations according to the present invention;

FIG. 3C is a front-view of a foot-therapy and toe-aligning device, illustrating a handle configuration according to the present invention;

DETAILED DESCRIPTION

The present invention relates to an exercise tool, and more particularly, to a foot-therapy and toe-aligning device that is devised to align, separate, treat, and stretch toes. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices may be shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

(1) Description of Various Aspects

Figure 1:
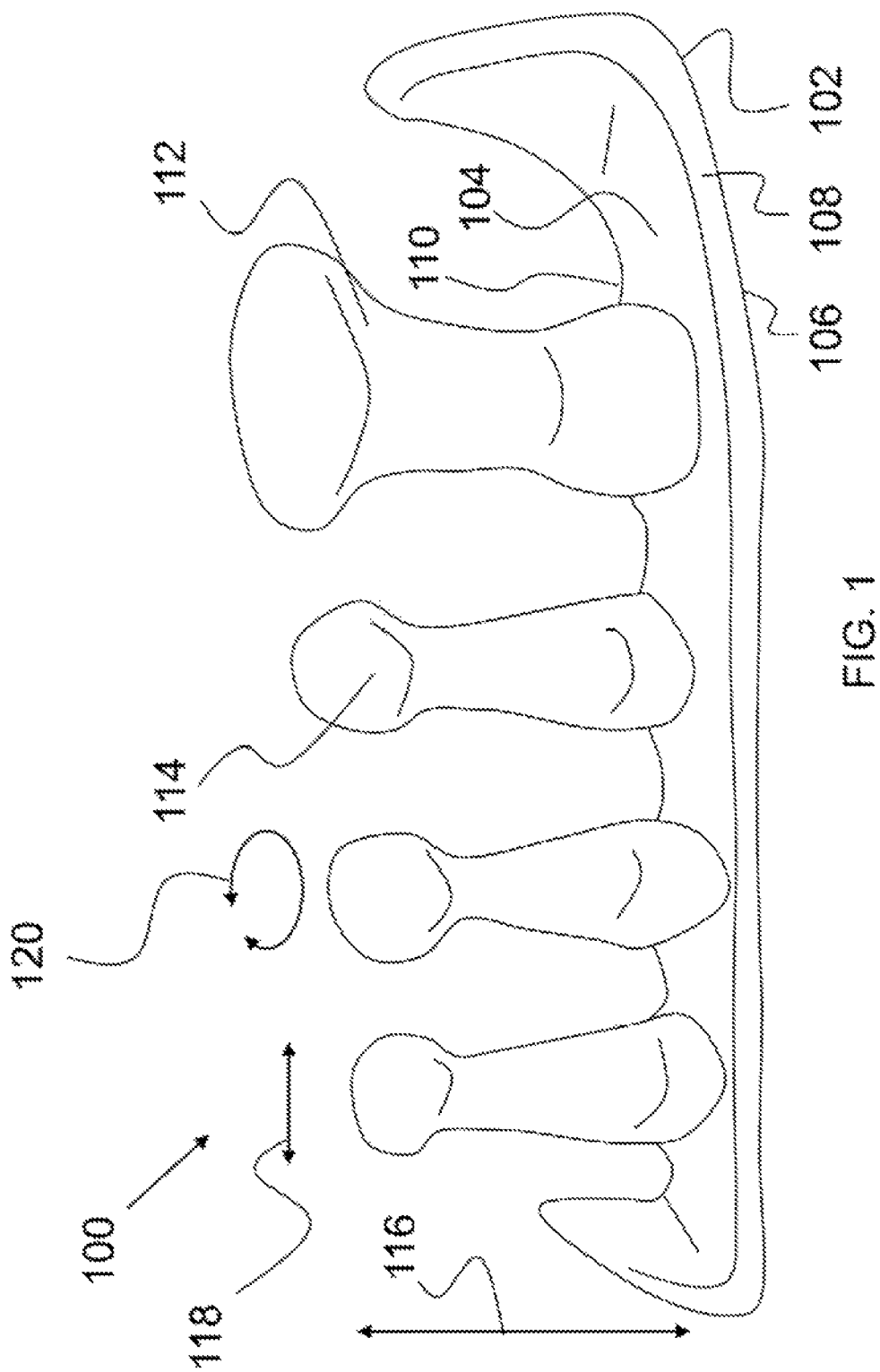
FIG. 1 is a front-view of a foot-therapy and toe-aligning device according to the present invention.

A foot-therapy and toe-aligning device 100 according to the present invention is shown in FIG. 1. The foot-therapy and toe-aligning device 100 comprises a frame 102 that allows for a post (described below) to become attached, embedded, or integrally formed thereto. The device 100 (including the frame 102) is constructed of any suitable material, a non-limiting example of which includes an elastic material (e.g., an elastomeric gel such as a polymer or any other suitable elastic material). Although the frame 102 can be formed of other materials, it is desirable that it is formed of an elastomeric material. Additionally, the frame 102 may be optionally inflatable or filled with a fluid. When inflatable, the frame 102 may be inflatable to various pressures. Furthermore, the frame 102 may be formed through any suitable means for forming a frame 102, non-limiting examples of which include injection molding, cast molding, compression molding, and extrusion molding. Further, the device (e.g., frame 102 and posts) are formed of a material (e.g., transparent material) that allows light to pass through the material. For example, the elastomeric gel is transparent such that a user can see into or through the frame 102 (and posts) and the device 100. The device 100 can be formed such that its transparency ranges from 100 percent to a being opaque.

The frame 102 includes a top portion 104, a bottom portion 106, a front portion 108, and a back portion 110. A plurality of posts 112 formed of an elastic material are connected with the frame 102 such that they extend from the top portion 104. A non-limiting example of the elastic/elastomeric material is a polymer elastic gel. Each of the plurality of posts 12 has an exposed outer edge 114. The posts 112 can be separately formed and attached with the frame 102 or, in another aspect, the posts 112 are integrally formed with the with the frame 102 through a single, injection-molding process where the frame 102 and posts 112 are separate in name only.

Figure 2:
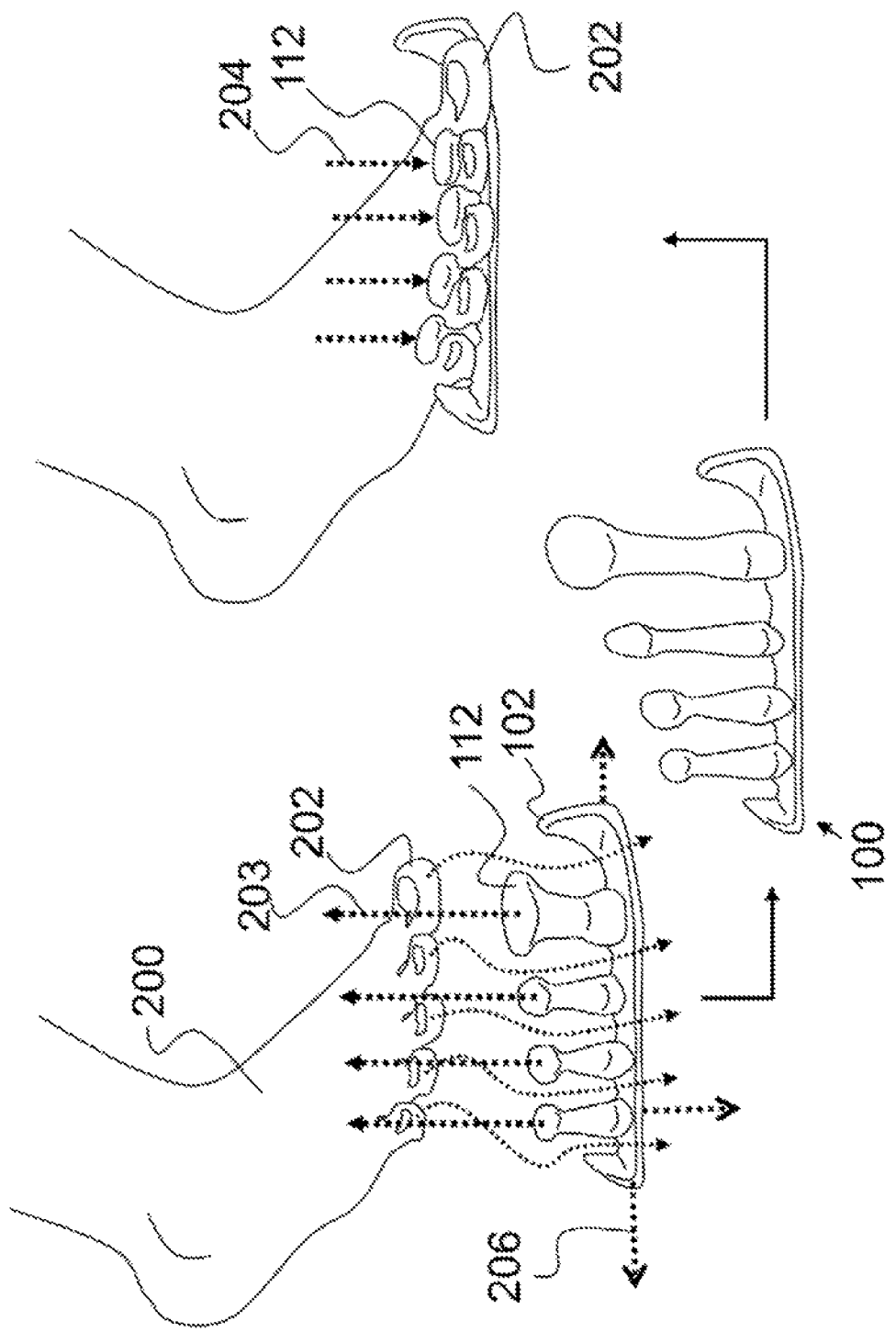
FIG. 2 is a front-view of a foot-therapy and toe-aligning device according to the present invention, illustrating the device being attached with a user's toes.

FIG. 2 illustrates a user 200 using the foot-therapy and toe-aligning device 100. As shown, a user 200 may place at least one of the plurality of posts 112 between their toes 202 and pull 203 the post 112 to stretch and elongate the post 112 between the toes 202. Upon release, the elastic/elastomeric material of the post 112 causes the post 112 to attempt to return 204 (contract) to its original shape. Because a toe 202 is placed between two adjacent posts 112, the post cannot return to its exact original shape, thereby causing portions of the post to expand out and conform its shape to, and fit, snugly against, the user's toes 202. For example, a top portion (and sometimes a bottom portion) of the post expands out to fit snugly against the toes 202.

The ability of the posts 112 to conform their shape to a user's toes 202 is a beneficial feature of the present invention. For example, the toe posts in the prior art are formed of a die-cut or pressure molded semi-rigid foam. Due to the nature of foam, foam does not allow for the required elongation and subsequent conforming shape of the toe posts, as applicable to the present invention. In other prior art, such as application '354, the outer edges of the toe posts are connected by a frame. Because the outer edges of the frame are connected, the toe posts in application '354 cannot be easily elongated and returned to conform their shape to the user's toes.

For further clarification, referring to FIG. 1, the toe posts 112 have a length 116, a diameter 118, and a circumference 120. Being formed of an elastomeric material causes the toe posts 112 to have properties such that stretching the toe posts 112 lengthwise 116 causes the toe posts 112 to become thinner in diameter 118 and thereby more easily placed between the user's toes. Upon release, a stretched toe post 112 would contract in length 116 and expand circumferentially 120 to conform tightly to and effectively hold the user's toes, thereby remaining in the desired position. In other words, when released, the post 112 expands its diameter 118 to increase pressure against the toes and thereby hold the device in the desired position. Equally significant, the posts 112 contract along a lengthwise 116 axis to impart a lengthwise 116 axis compressive holding force on the surface of the toe as well, also holding the device in the desired position. The forces resulting from contraction and elongation, individually and in combination, easily enable a user to place, affix and maintain a toe post 112 position between a user's toes.

Thus, the elastomeric material of the toe posts 112 of the present invention provides a benefit that allows the foot therapy and toe-aligning device 100 to be easily applied to a user's toes 202 by being elongated and then placed individually between adjacent toes 202. The toe post 112 can be positioned fore and aft between the toes 202 to allow for user-specific placement and positioning. Thereafter, upon release, the elastomeric material of the toe post 112 causes the toe post 112 to conform its shape to the user's toes 202 and to be positioned and maintained at numerous locations between the user's toes 202 for customizable positioning. To provide this effect, the toe posts 112 are formed of an elastomeric polymer that has sufficient elastomeric properties. For example, if the toe posts 112 are too soft, then they will not provide a therapeutic benefit of separating adjacent toes 202. Alternatively, if the toe posts 112 are too hard (e.g., hard plastic), then they will not allow the toe posts 112 to be stretched and released to be conformed to the user's toes 202. As a non-limiting example, the toe posts 112 are desirably formed of an elastomeric material having the following properties: hardness between 20 and 90 on the Shore 00 scale for product comfort; elongation between 50% and 1000% for product functionality; and tensile strength between 100 and 2000 pounds per square inch (psi). More specifically, the toe posts 112 are formed of an elastomeric material having the following properties: hardness between 35 and 80 on the Shore 00 scale; elongation between 50% and 800%; and tensile strength between 100 and 800 psi. As can be appreciated by one skilled in the art, the above ranges are for exemplary illustrative purposes only and are not intended to limit the present invention thereto.

As shown in the figures, the toe posts 112 are formed in any suitable ergonomic shape, non-limiting examples of which include being conically and/or cylindrically shaped. The toe post 112 is formed in a shape to provide a therapeutic benefit in combination with the properties of the elastomeric material. For example, in certain circumstances, a thicker toe post 112 would benefit from a softer elastomeric material. Alternatively, a thinner toe post 112 would benefit from harder elastomeric material.

It should be noted that the description above with respect to the elastomeric material of the toe posts 112 is also applicable to the frame 102. For example, the frame 102 can also be formed of an elastomeric material that includes all of the elastomeric properties listed above. Thus, the frame 102 is formed to also provide for extension and compression forces. In this aspect, the frame 102 can be stretched 206 along a lateral axis to allow a user to position the frame 102 against the user's 200 foot. Upon release of the stretched frame 102, the frame 102 contracts in an attempt to return to its original shape which causes the frame 102 to snuggly hold the toes 202 in place along the lateral axis of the frame 102.

Figure 3A:
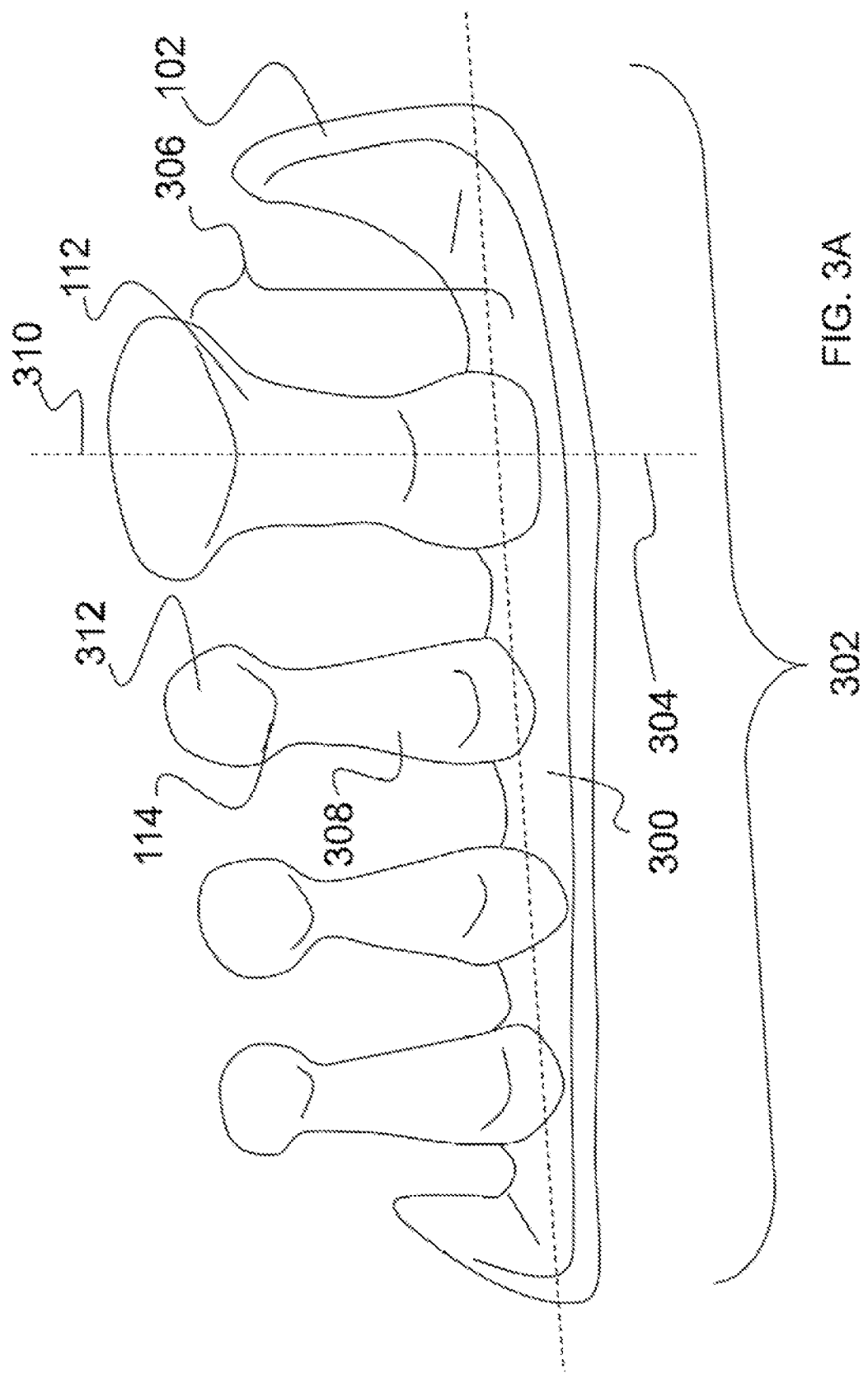
FIG. 3A is a front-view of a foot-therapy and toe-aligning device according to the present invention.

As shown in FIG. 3A, the frame 102 has an outer frame surface 300, a frame length 302, and a center frame-axis 304 running the frame length 302. Additionally, each of the plurality of posts 112 has a length 306, an outer post surface 308, and a center post axis 310 running the post length 306. The material forming the frame 102 and posts 112 is formed to have a consistent density throughout the frame 102 and posts 112 respectively. In another aspect, the elastomeric material forming the posts 112 has a compression resistance and a density that varies from the outer post surface 308 to the center post axis 310 (as a non-limiting example, the density is greater at the center post axis 310 and decreases toward the outer post surface 308). In yet another aspect, the elastomeric material forming the frame 102 has a compression resistance and density that varies from the outer frame surface 300 to the center frame axis 304 (as a non-limiting example, the density is greater at the center frame axis 304 than the outer frame surface 300). The compression resistance is softer on the outside and harder on the inside of each of the respective locations. Alternatively, the compression resistance can be harder on the outside and softer on the inside.

To assist a user in stretching each post 112, each post 112 includes a handle 312 connected with the outer edge 114. The handle 312 can be formed as the outer edge 114 itself, or formed separately and attached with the outer edge 114. As a non-limiting example, the outer edge 114 of the toe post 112 is formed in a bulbous shape to operate as a handle 312. The handle 312 allows a user to easily stretch and elongate the post 112.

FIG. 3B illustrates additional integral and attached handle configurations according to the present invention. For example, the handle can be an integrally formed ring 314 that is formed at the outer edge 114 of the post 112. As can be appreciated by one skilled in the art, an example of such a process for forming an integrally formed ring 314 is one-piece injection molding. Using a ring-shape, a user can insert a finger into or grasp the ring to stretch the post 112. In another aspect, the handle can be a fused ring 316 that is separately formed and fused to the outer edge 114 of the post 112 using standard material fusing techniques (e.g., melting and gluing). In yet another aspect, the handle can be a solid ring 318 that is attached with an anchor 320 that is disposed within the post 112. For example, the solid ring 318 can be formed of a stiff material such as a hard plastic or metal that allows a user to grasp the handle and stretch the post 112, with the anchor 320 pulling up upon the outer edge 114. As can be appreciated by one skilled in the art, the handle is any suitable shape to allow a user to hold and stretch the post 112. For example, the handle can also be formed as a solid bar 322 that is attached with an anchor 320 disposed within the post 112.

FIG. 3C illustrates yet another handle configuration. In this aspect, the handle 312 is connected with the outer edge 114 of each of the plurality of posts 112. The handle 312 can be integrally formed with the posts 112, or formed as a separate item and attached with the posts 112 (either externally using an attachment mechanism (as described below) or internally). For example, the handle 312 can be connected with an anchor 320 that is disposed within each of the posts 112.

Figure 4:
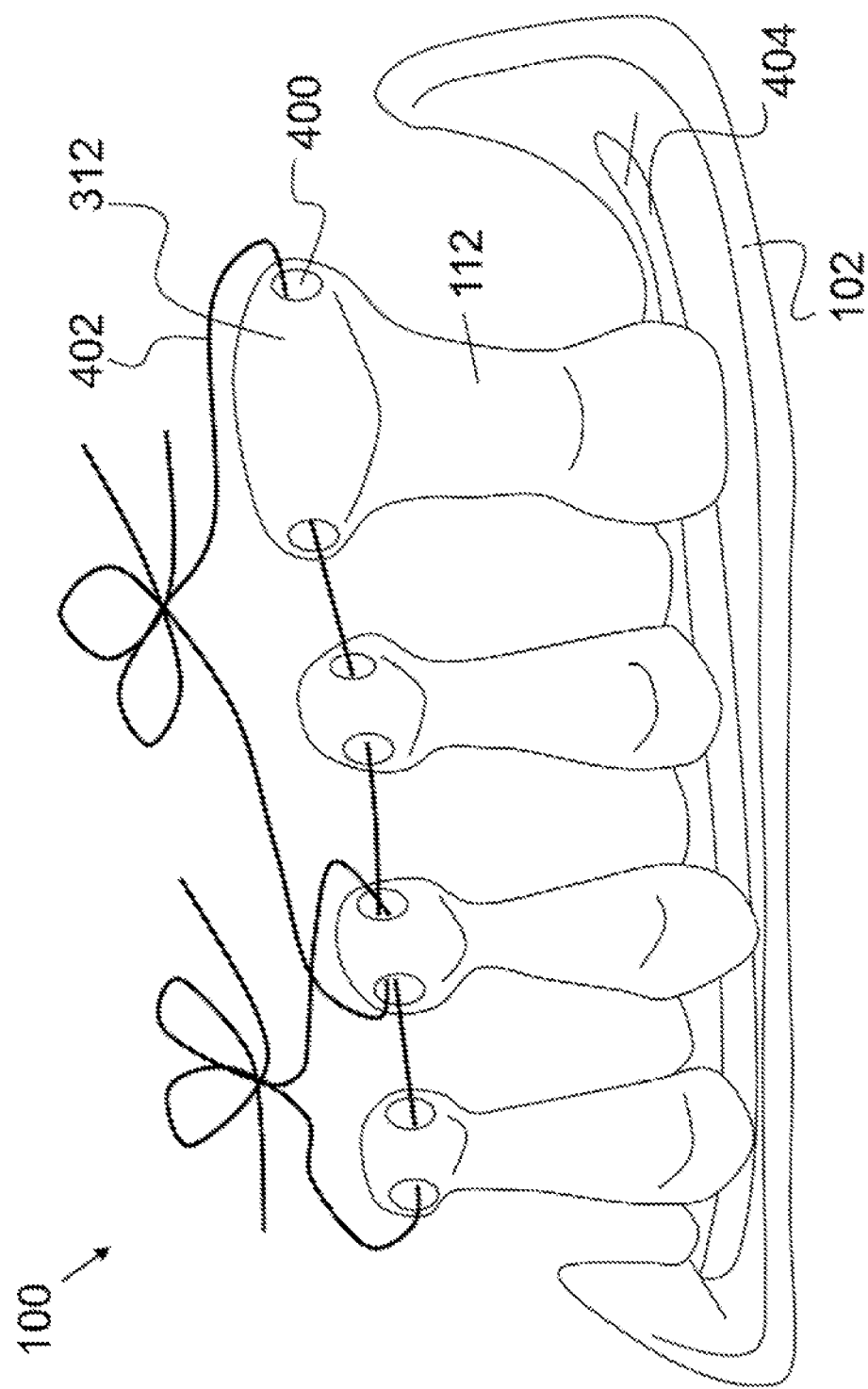
FIG. 4 is a front-view of a foot-therapy and toe-aligning device according to the present invention, illustrating holes formed through a plurality of posts.

As shown in FIG. 4, the handles 312 optionally include an attachment mechanism 400, allowing a user to connect the handles 312 using a connector 402 that connects the attachment mechanism 400. The attachment mechanism 400 is any suitable mechanism or device that allows for connection with the connector 402, a non-limiting example of which includes holes formed through the handles 312. The connector 402 is any suitable mechanism or device that can be connected with the attachment mechanism 400 to allow a user to connect the handles 312, non-limiting examples of which include a thread and cord.

In some applications, it is desirable to have an integral flexible frame 102, such as that formed entirely of an elastomeric material. In other applications, it may be desirable to have a frame 102 that has an increased rigidity. As such, in another aspect, a rigid material 404 is positioned within the frame 102 to provide a rigid support for the frame 102. The rigid material 404 is any suitable mechanism or device for providing a rigid support for the frame 102, a non-limiting example of which includes a rigid rod, such as a plastic rod.

Figure 5:
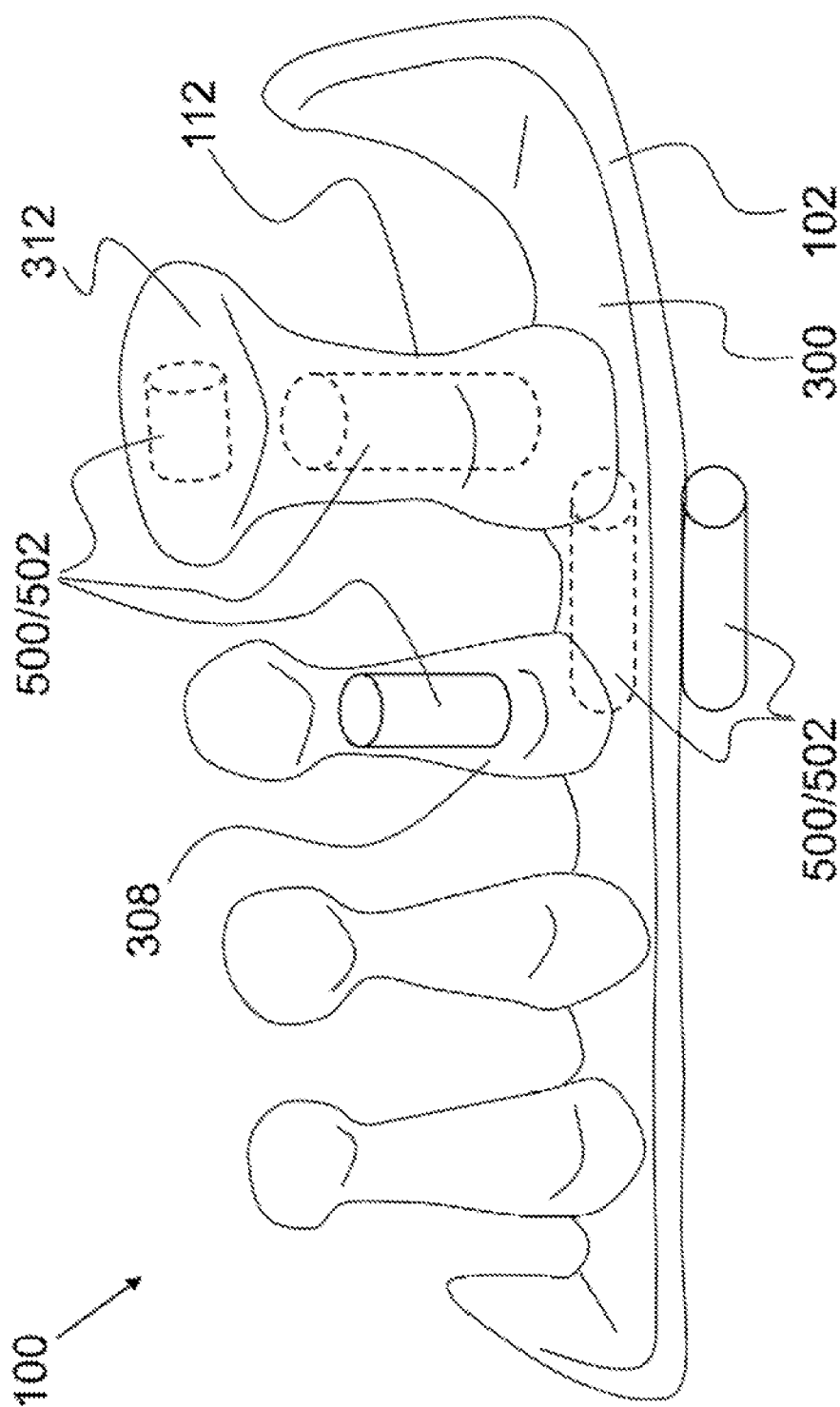
FIG. 5 is a front-view of a foot-therapy and toe-aligning device according to the present invention, illustrating an electronic device being connected with the foot-therapy and toe-aligning device.

As shown in FIG. 5, to provide additional therapeutic benefits to a user, an electronic device 500 is attached with the foot-therapy and toe-aligning device 100. The electronic device 500 is attached with the foot-therapy and toe-aligning device 100 in any suitable manner to provide a desired therapeutic benefit, non-limiting examples of which include being positioned within a post 112, being attached with the outer post surface 308 of the post 112, being positioned within an interior of the frame 102, being attached with the outer frame surface 300 of the frame 102, and being attached with a handle 312 (interior and/or exterior).

The electronic device 500 is any suitable mechanism or device for providing a therapeutic benefit, non-limiting examples of which include a vibrating mechanism for massaging and stimulating a user's toes, a light system (e.g., light-emitting diode, near infra-red), a heating system (e.g., heating element), a cooling system, a sensor, and a pulsating pressure mechanism. The sensor is any suitable mechanism or device capable of sensing something, non-limiting examples of which include a pressure sensor, a light sensor, and a temperature sensor.

When a sensor is included, the sensor is configured to provide feedback when a predetermined threshold is reached. For example, if the sensor is a pressure sensor, the sensor may create a sound when a certain amount of pressing pressure is reached. As another non-limiting example, if the electronic device 500 is a heating element, an alarm may be sounded when the temperature reaches a certain degree. The feedback is any suitable feedback for alerting a user, or third party, that the predetermined threshold has been met, non-limiting examples of which include light, sound, vibration, and temperature (e.g., change in temperature). In other words, the feedback is any suitable feedback that can be received and interpreted by a user or a third party.

As can be appreciated by one skilled in the art, the electronic device 500 requires a power source. The power source may be included within the device, or maintained externally and electrically connected with the electronic device 500.

In another aspect, a magnet 502 is attached with the foot-therapy and toe-aligning device 100 to provide a therapeutic benefit. The magnet 502 is attached with the foot-therapy and toe-aligning device 100 in any suitable manner, non-limiting examples of which include being positioned within a post 112, being attached with the outer post surface 308 of the post 112, being positioned within an interior of the frame 102, being attached with the outer frame surface 300 of the frame 102, and being attached with a handle 312. For illustrative purposes with respect to FIG. 5, the magnet 502 is interchangeable with the electronic device 500.

Figure 6:
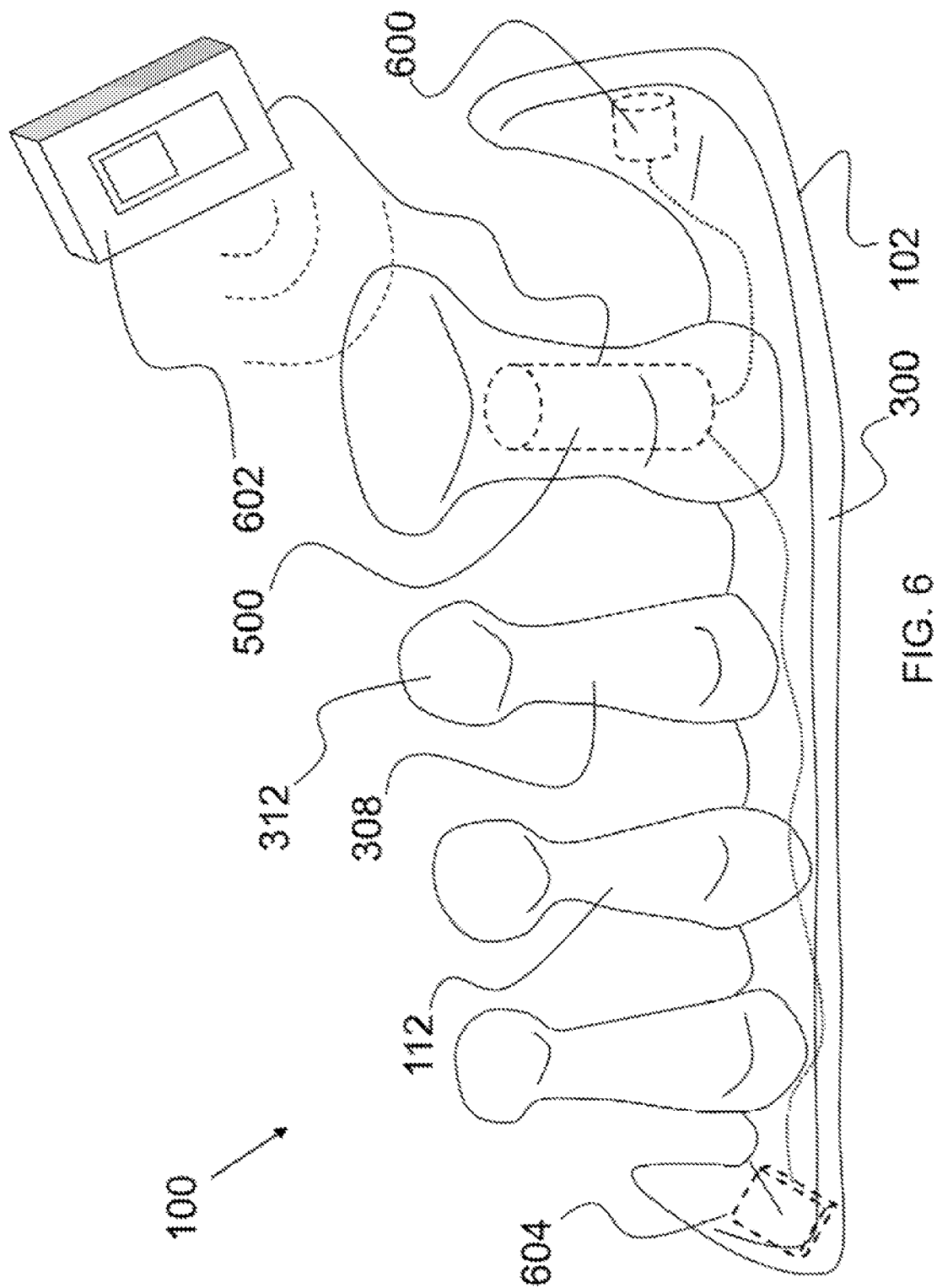
FIG. 6 is a front-view of a foot-therapy and toe-aligning device according to the present invention, illustrating a motion sensor and a remote control being connected with the electronic device.

As shown in FIG. 6, the electronic device 500 can be controlled through a variety of techniques. For example, a motion sensor 600 may be connected with electronic device 500 to actuate the device 500. In this aspect, the device 500 is turned on when the motion sensor 600 detects motion. As another example, a remote control 602 is connected with the electronic device 500 to allow a user to selectively control the electronic device 500, such as by turning it on, off, up, down, and to a time-cycle. The up and down controls relate to functions as applicable to certain electronic devices 500, such as when the electronic device is a heating element or a vibrating mechanism. Additionally, the remote control 602 can be either wired or wireless.

With the advent of new computer technologies, it may be desirable to control the electronic device 500 via a computer (i.e., processing unit). In this aspect, the remote control 602 is a processing unit that can operate the electronic device 500. For example, certain computer-controlled therapeutic programs can be operated and controlled via the processing unit. As a specific non-limiting example, a massage therapy program can be used to control the vibrating mechanism, where it increases and decreases the vibrating strength of the vibrating mechanism according to a particular massage therapy program.

Figure 17:
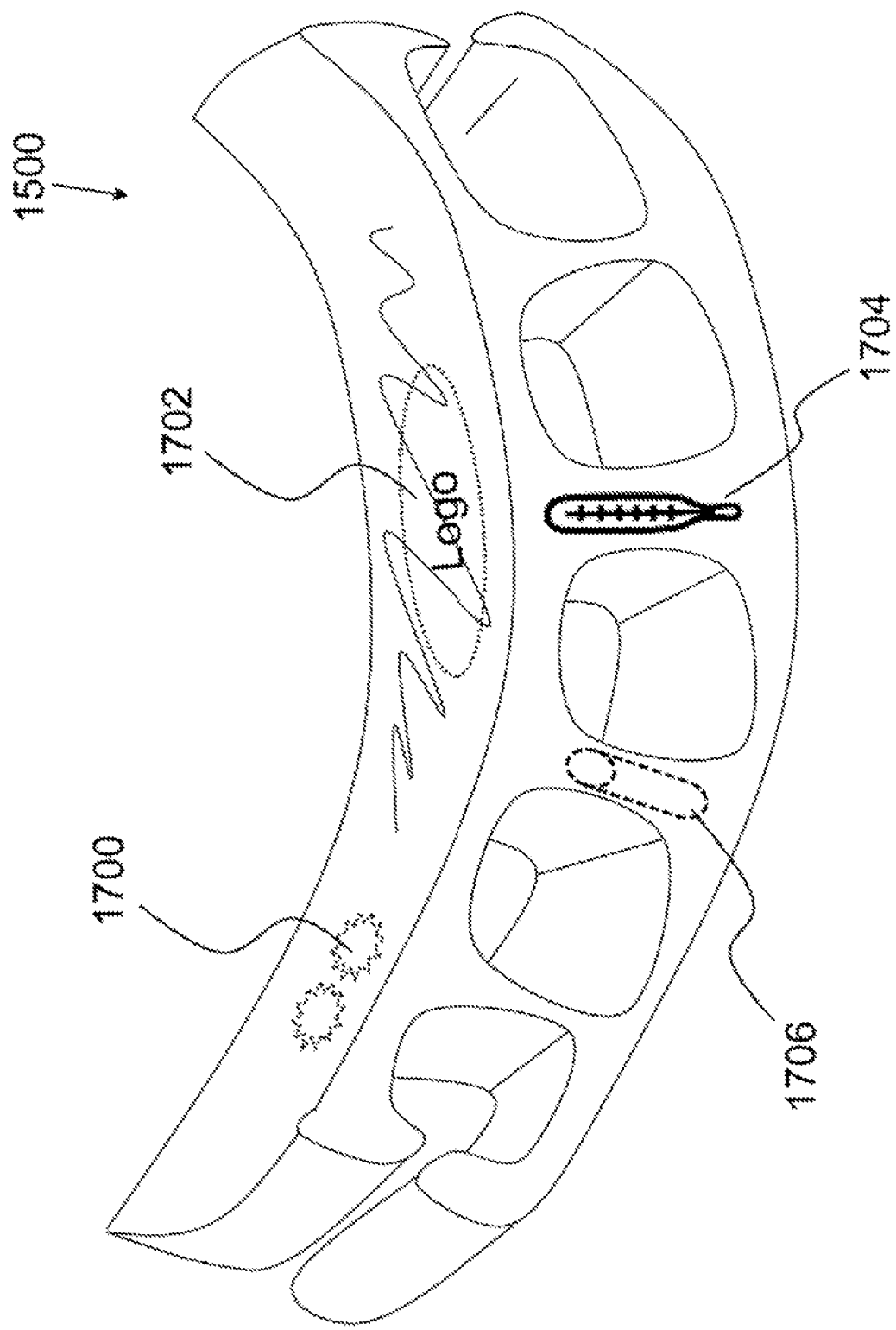
FIG. 17 is an illustration of a foot-therapy and toe-aligning device according to the present invention, illustrating implantation elements implanted within the device.

In addition to controlling the electronic device 500, the processing unit can be used to monitor and control the biological functions of the user. For example, the processing unit can be connected to a temperature sensor (e.g., a thermometer, as illustrated in FIG. 17) to monitor the user's temperature. If the user's temperature falls outside a predetermined range of temperatures, the processing unit can turn on a heating or cooling system, as appropriate, to heat/cool the user. As can be appreciated by one skilled in the art, such a monitoring and control feature can also be used to monitor and control external conditions and devices, or other electronic devices, such as lights and a vibrator mechanism.

In yet another aspect, a computer controller chip 604 can be connected with the foot-therapy and toe-aligning device 100 itself. As was the case above, the chip 604 is electronically connected with the electronic device 500 and is used to control the electronic device 500. The chip 604 is connected with the foot-therapy and toe-aligning device 100 at any suitable location, non-limiting examples of which include being positioned within a post 112, being attached with the outer post surface 308, being positioned within an interior of the frame 102, being attached with the outer frame surface 300 of the frame 102, and being attached with a handle 312.

Figure 7:
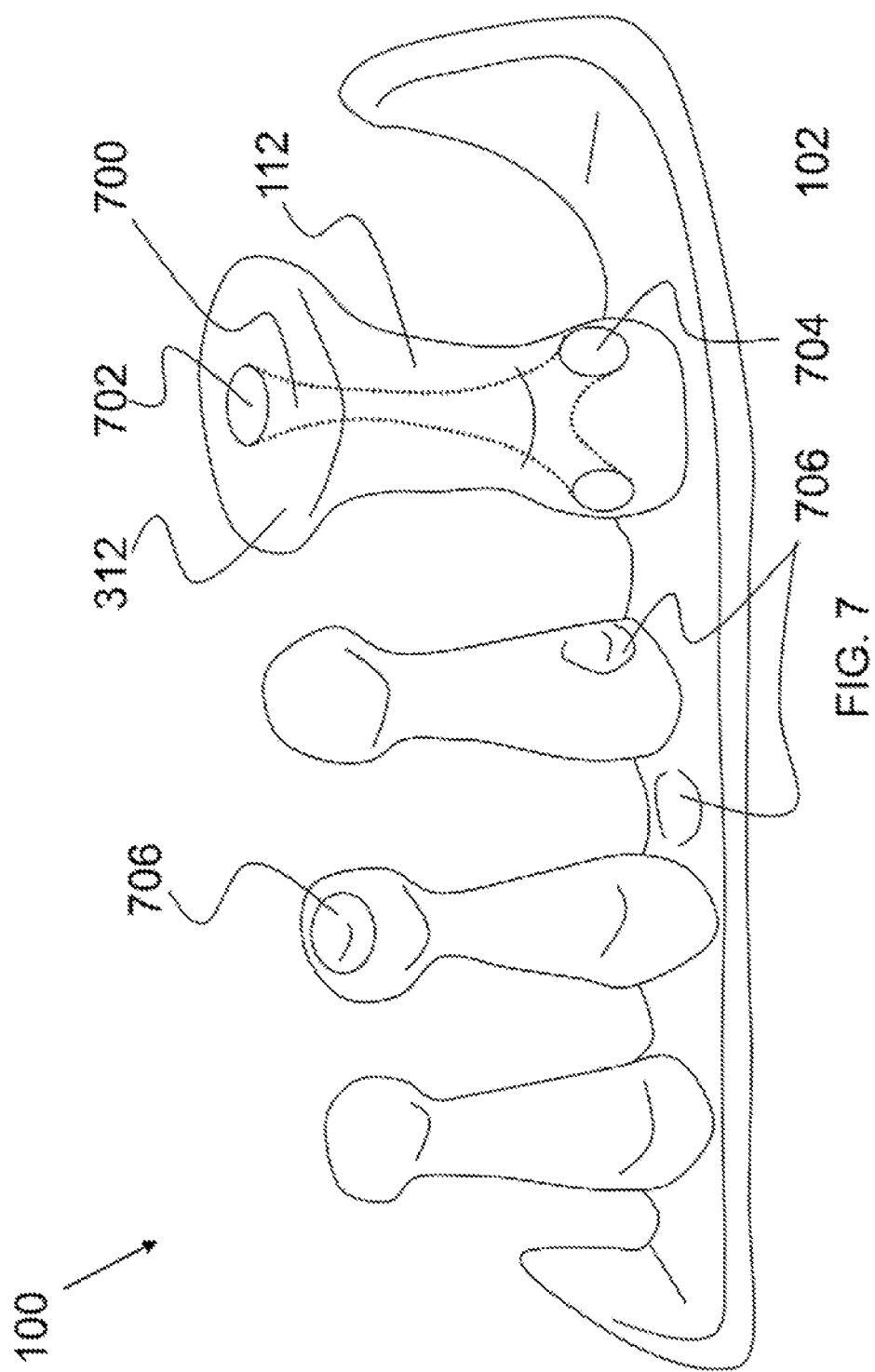
FIG. 7 is a front-view of a foot-therapy and toe-aligning device according to the present invention, illustrating a port being formed through a post, and a reservoir being formed on the foot-therapy and toe-aligning device.

In another aspect, it may be desirable to apply a material (such as a lotion or medicinal cream) to the foot-therapy and toe-aligning device 100 for dispersal around a user's foot. As shown in FIG. 7, a port 700 is formed through at least one of the plurality of posts 112 and/or frame 102. The port 700 is formed in any suitable manner to allow a user to insert a material into the port 700 for dispersal proximate a user's toes. For example, the port 700 may have an inlet 702 formed in the handle 312, with an outlet 704 formed in the post 112 such that material inserted within the inlet 702 is dispersed to the user's toes at the outlet 704.

The material may be applied to the user's foot through a variety of techniques. For example, a reservoir 706 is formed in the foot-therapy and toe-aligning device 100 such that a user may position a material into the reservoir 706. The reservoir 706 is formed at any suitable location on the foot-therapy and toe-aligning device 100, non-limiting examples of which include being formed in the outer post surface 308, being formed in the outer frame surface 300, and being formed in the handle 312. The reservoir 706 is formed in any suitable shape to hold the material. For example, the reservoir 706 may be a simple divot, or may include ribs. The reservoir 706 can be used to hold materials externally to be delivered on or through the device 100, non-limiting examples of such materials include scented liquids, lotions, powders, and medicinal products (such as treatment products for athlete's foot).

In another aspect, any outer surface of the device 100 may include traction members (not shown) to increase the contact surface area of the area in which the traction members are formed. The traction members improve the traction characteristics between the device 100 and the user. For example, the traction members may be ribs, bumps, notches, etc., to cause the device to better grip another surface. By way of example, the posts include traction members to assist the post in affixing with an adjacent toe.

Figure 8:
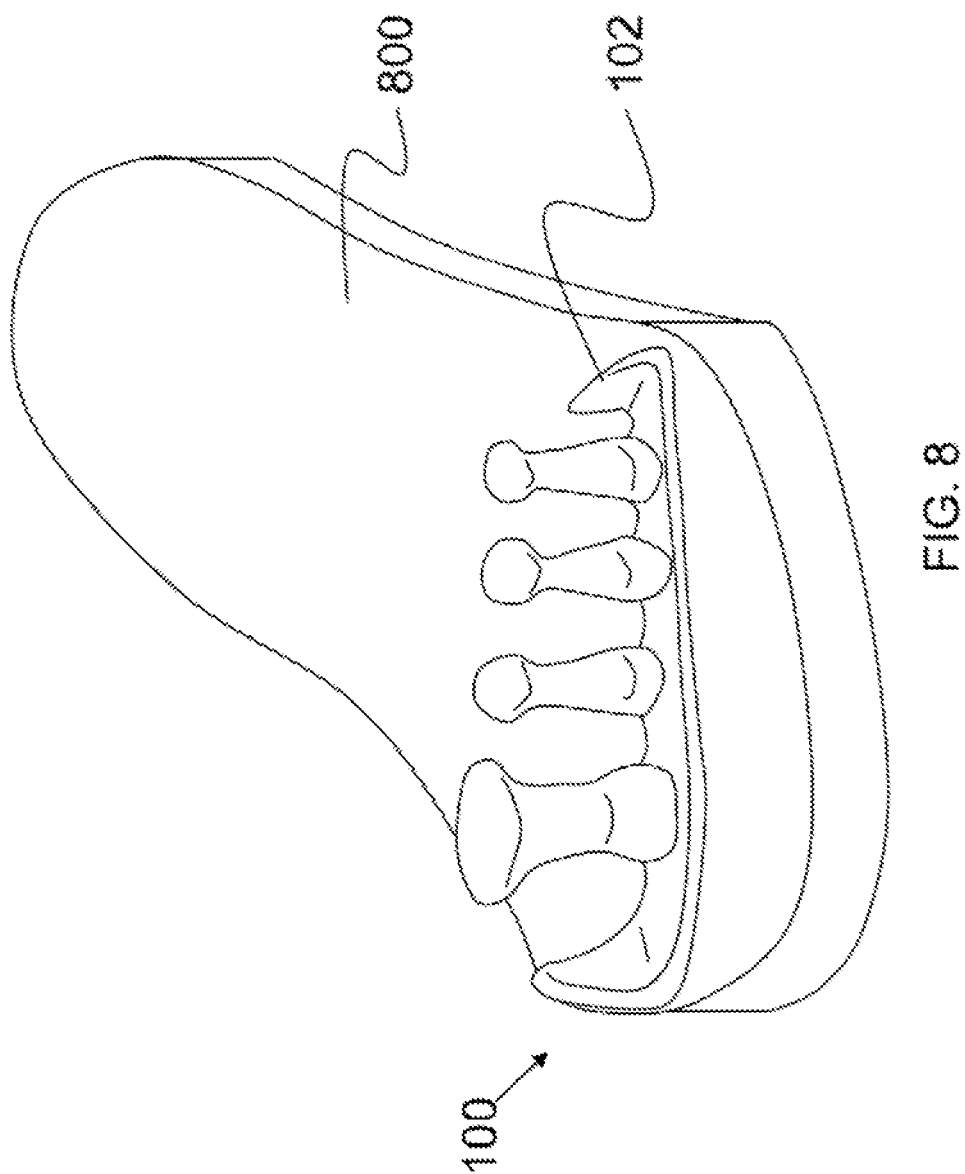
FIG. 8 is a front-view of a foot-therapy and toe-aligning device according to the present invention, illustrating the foot-therapy and toe-aligning device being attached with a footwear.
Figure 9:
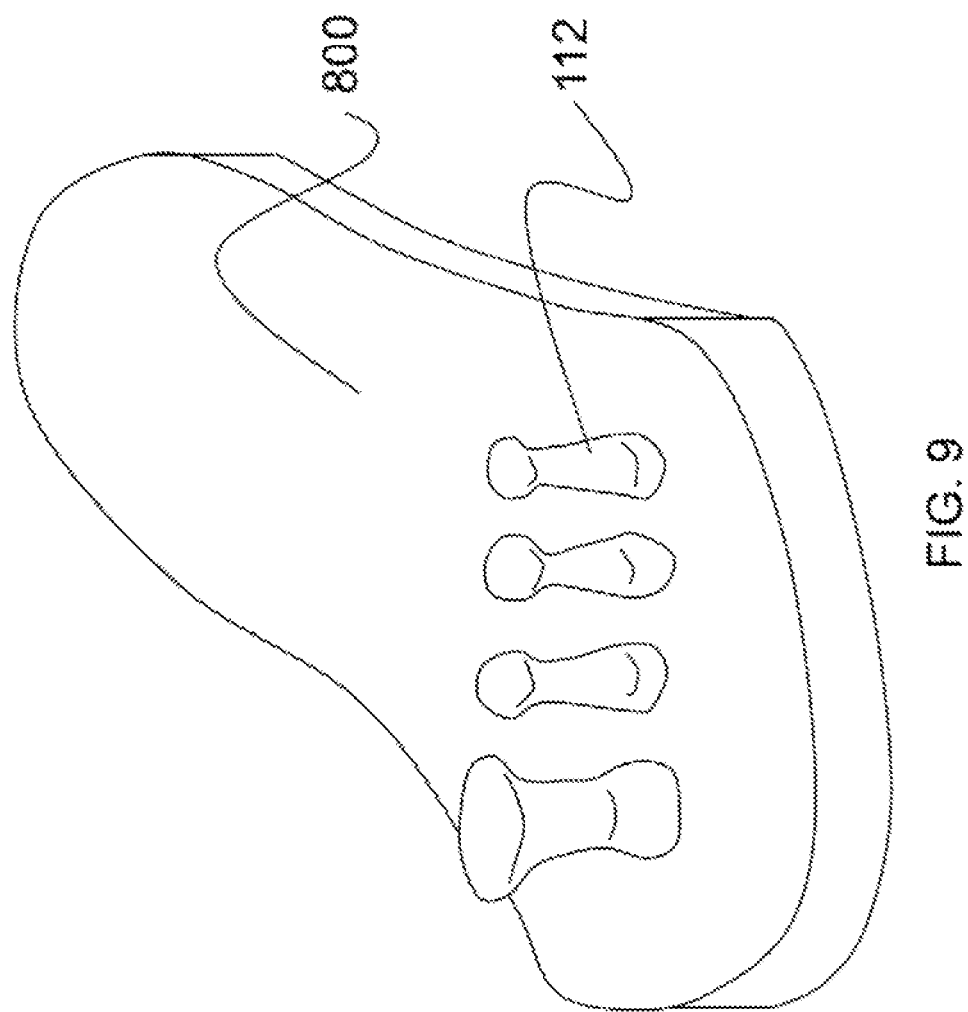
FIG. 9 is a front-view of a foot-therapy and toe-aligning device according to the present invention, illustrating the foot-therapy and toe-aligning device being integrally formed with the footwear.

In another aspect, the foot-therapy and toe-aligning device 100 can be incorporated into footwear through a variety of techniques. As shown in FIG. 8, a piece of footwear 800 is attached with the frame 102. Alternatively, as shown in FIG. 9, the piece of footwear 800 can operate as the frame, with the posts 112 protruding from the piece of footwear 800.

Figure 10:
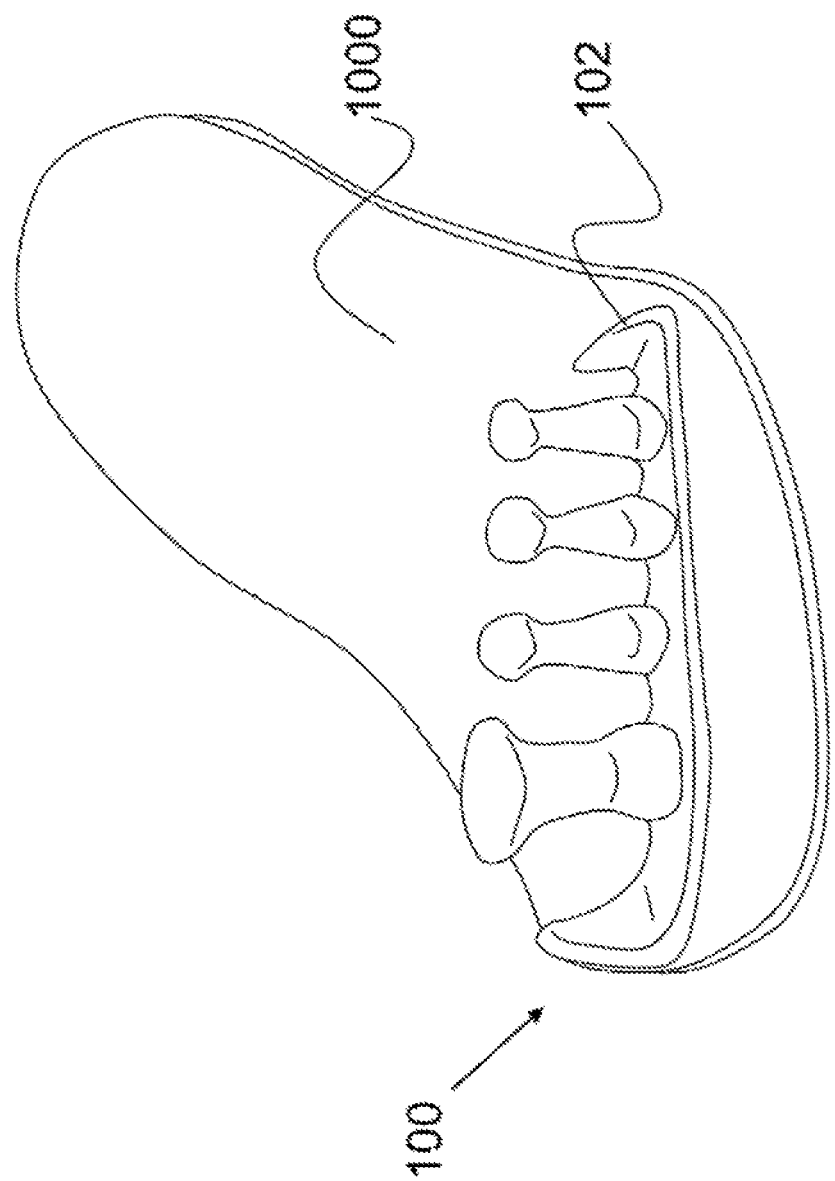
FIG. 10 is a front-view of a foot-therapy and toe-aligning device according to the present invention, illustrating the foot-therapy and toe-aligning device being attached with a shoe insole.
Figure 11:
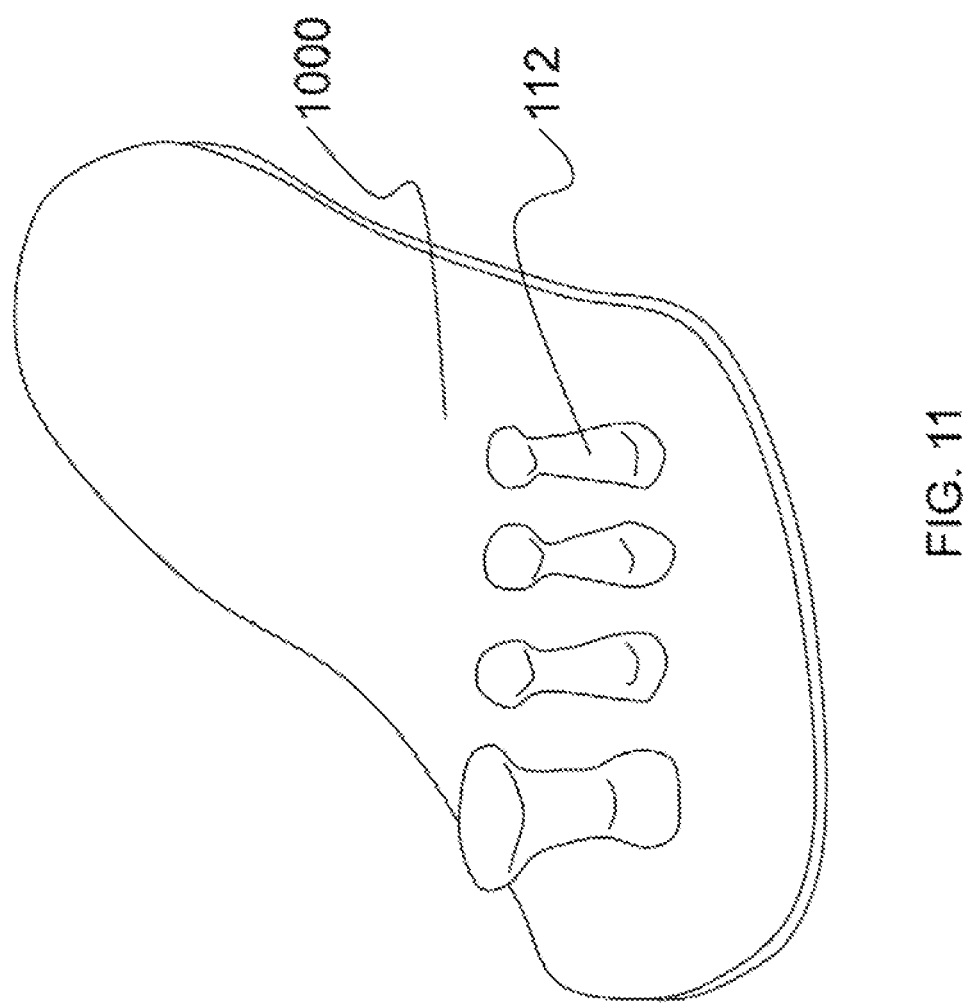
FIG. 11 is a front-view of a foot-therapy and toe-aligning device according to the present invention, illustrating the foot-therapy and toe-aligning device being integrally formed with shoe insole.

In yet another aspect, the foot-therapy and toe-aligning device 100 can be incorporated into a shoe sole insert. As shown in FIG. 10, a shoe sole insert 1000 is attached with the frame 102, thereby allowing a user to place the foot-therapy and toe-aligning device 100 within a shoe and wear the shoe while treating the user's toes. Alternatively, as shown in FIG. 11, the shoe sole insert 1000 can operate as the frame, with posts 112 attached with and protruding from the shoe sole insert 1000. Another example of such a configuration would be an enlarged frame that includes a sufficient number of posts 112 for both feet (e.g., 8 posts) with the posts appropriately positioned to allow for placement of both feet upon the enlarged frame. In this aspect, the enlarged frame would act as a platform where both feet are held in place upon it using a combination of the platform and toe posts 112. Such an aspect would be beneficial, for example, for holding both feet in place during a foot bath.

Figure 12:
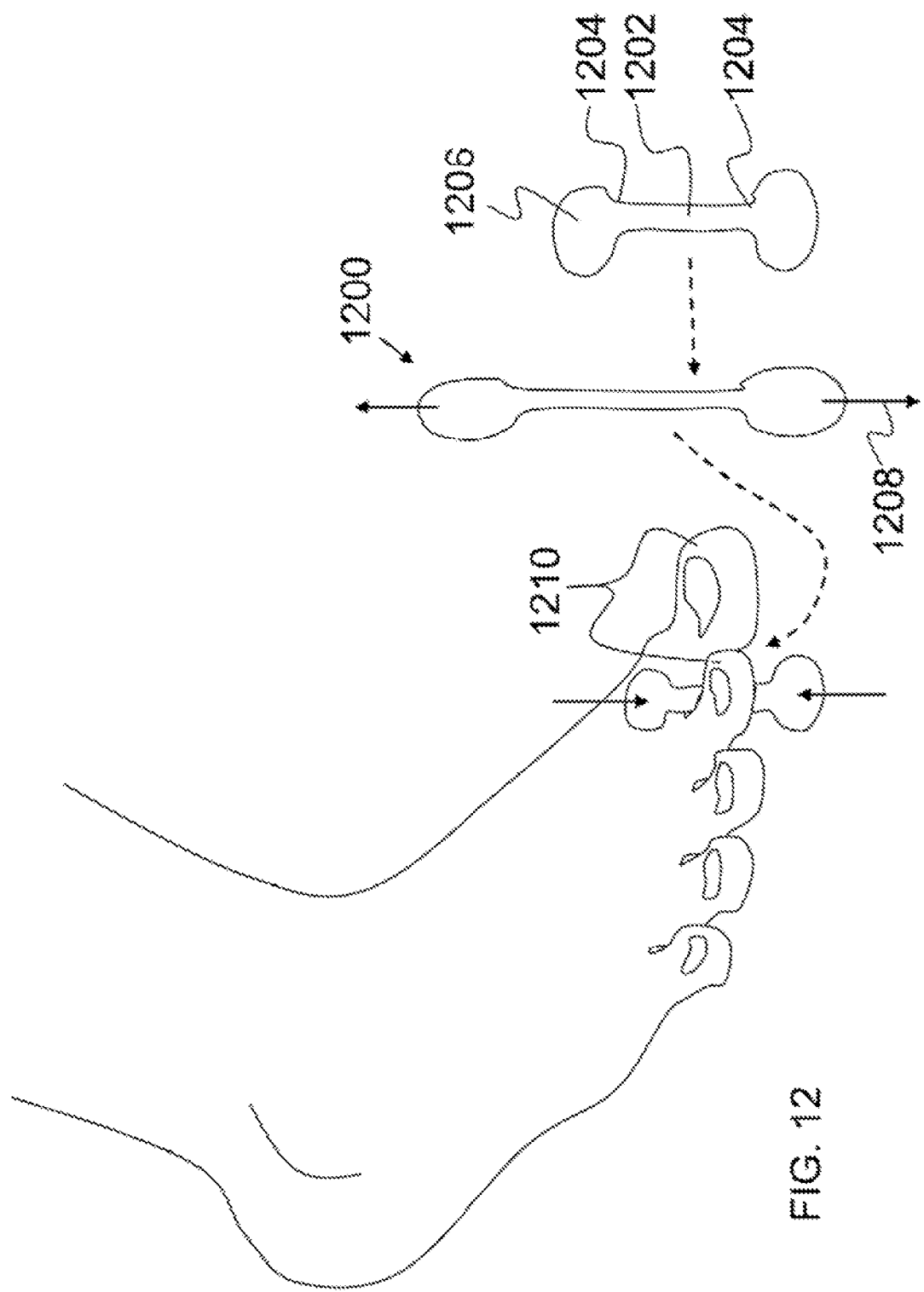
FIG. 12 is an illustration of another aspect of a foot-therapy and toe-aligning device according to the present invention, where the foot-therapy and toe-aligning device is formed as a dumbbell shaped post.

As described above, the foot-therapy and toe-aligning device includes a plurality of posts attached with some form of a frame. However, the invention is not intended to be limited thereto and can include additional aspects, such as that shown in FIG. 12. FIG. 12 illustrates another aspect of the foot-therapy and toe-aligning device 1200. In this aspect, the foot-therapy and toe-aligning device 1200 comprises an elongated post 1202 formed of an elastomeric material. The elongated post 1202 has two opposing edges 1204 with handles 1206 attached at each of the two opposing edges 1204. The handles 1206 may be separately formed and attached with the elongated post 1202, or integrally formed as a single piece. A user may use the handles 1206 to stretch 1208 the elongated post 1202 and place the now stretched elongated post 1202 between two adjacent toes 1210. Upon release, the elastomeric material of the post 1202 causes the post 1202 to conform its shape to fit snugly against the user's toes 1210.

Figure 13:
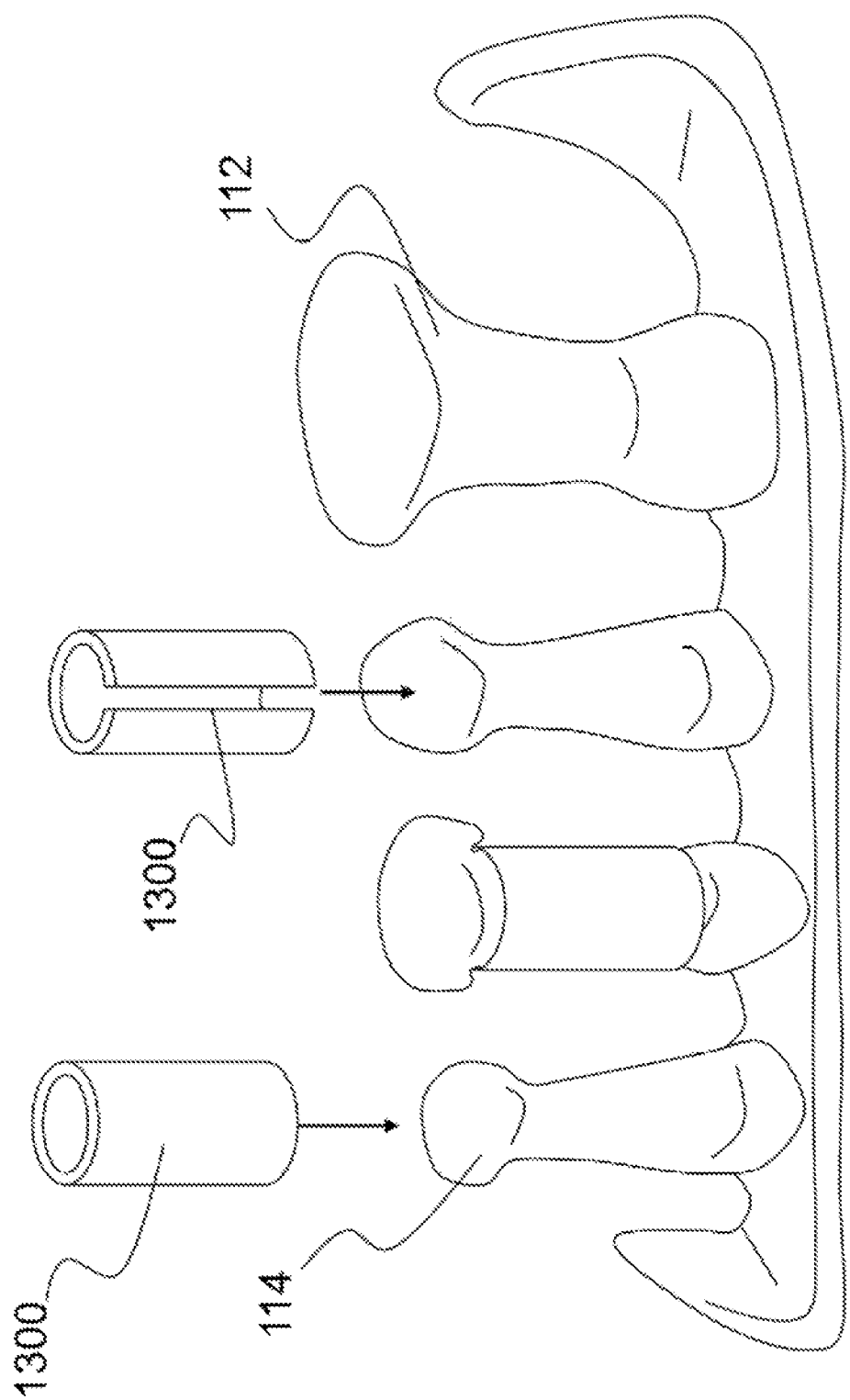
FIG. 13 is an illustration of a sleeve for covering a toe post according to the present invention.

FIG. 13 illustrates another aspect of the present invention where a sleeve 1300 is formed to fit over at least one of the toe posts 112. The sleeve 1300 is generally formed in any suitable shape to contain a toe post 112 therein. For example, the sleeve 1300 is generally cylindrical. Additionally, the sleeve can be formed of an elastomeric material so that it is expandable to conform to the shape of the post 112. The sleeve 1300 can be a continuous or split sleeve 1302. The split sleeve 1302 allows a user to open the sleeve for easy positioning over the post 112. The sleeve allows a user to customize the therapeutic action of the present invention and to deliver medication, cream, magnets, scent, etc. to a user's toes. For example, a user can insert a cream within the sleeve such that the cream is dispersed around the edges of the sleeve to a user's toes. The sleeve can also be formed to hold other devices (non-limiting examples of which include a vibrator or orthopedic pad for the ball of user's foot, etc.) to further treat and accommodate each individual's unique biometric characteristics. In another aspect, the sleeve itself can operate as a medicinal delivery mechanism for delivering a medication to a user. As a non-limiting example of such a mechanism, the sleeve can include the medications typically used in a non-smoking transdermal patch. Alternatively, the sleeve can operate as a base for placement of other medicinal systems. As a non-limiting example, the sleeve is formed to operate as a base for placement of an adhesive non-smoking transdermal patch upon the sleeve, thereby allowing for medical benefits.

It should be noted that the various medicinal delivery systems (reservoir, port, sleeve, etc.) described herein are not limited to the posts and can be formed and applied at any desirable portion of the device, such as within the holes, along the base, or at any other portion of the device. Thus, using the present invention, a user can wear the device while simultaneously applying a myriad of creams, lotions, powders, medicines, etc.

When disposable, such a disposable post cover would allow multiple people to use the present invention without fear of cross-contamination from other users. Additionally, the sleeve 1300 can be used to hold and transport a product to the toes, non-limiting examples of such a product include an anti-fungal cream, an anti-bacterial agent, and/or a moisturizing material. In another aspect, the sleeve 1300 itself can be impregnated with the product.

Figure 14:
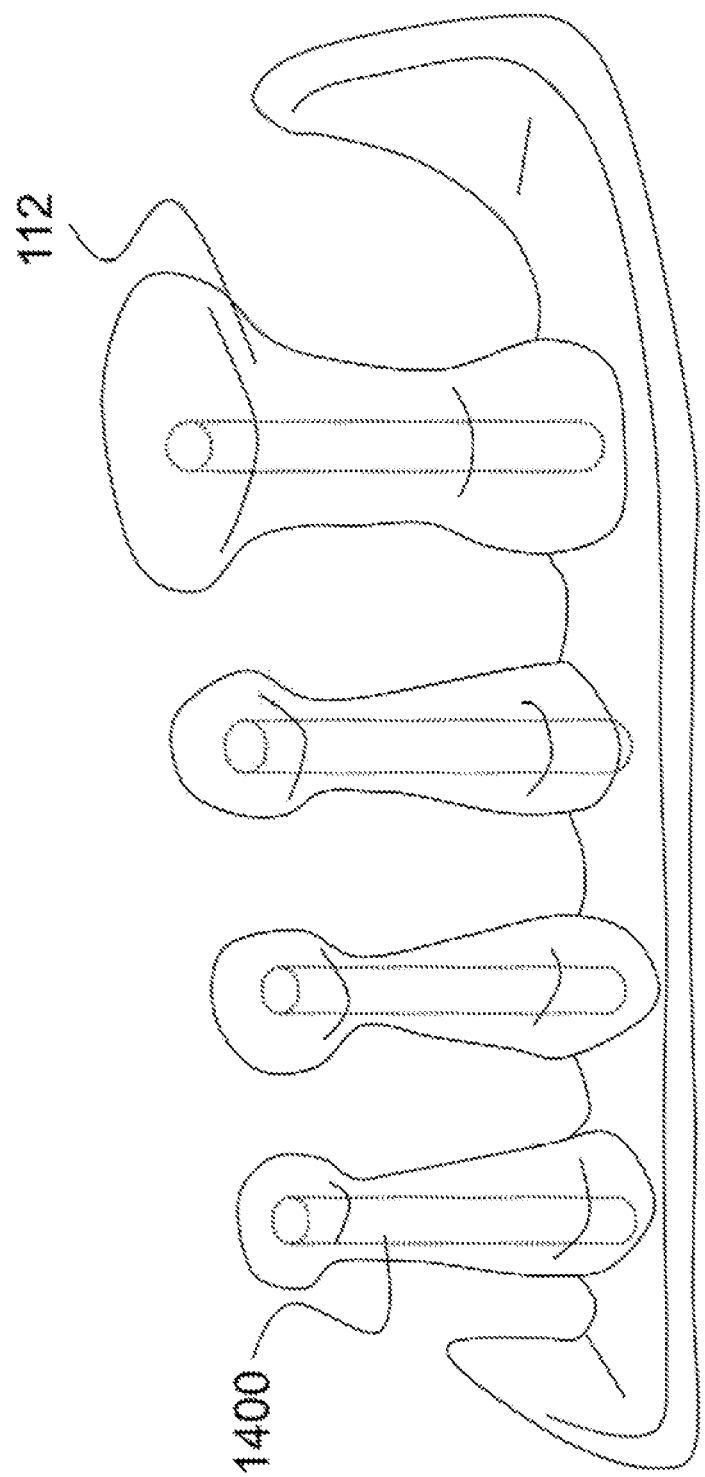
FIG. 14 is an illustration of the foot-therapy and toe-aligning device according to the present invention, with a support structure disposed therein.

FIG. 14 illustrates another aspect of the present invention. A support structure 1400 can be disposed within the toe posts 112 to provide the toe posts 112 with a rigid (or bendable/articulating) support. The support structure 1400 is any suitable rigid material, non-limiting examples of which include a metal rod and a plastic rod. The support structure 1400 can be disposed within the toe posts 112 individually such that they are not interconnected, or they can be connected through attachment with the rigid material shown in FIG. 4.

Figure 15:
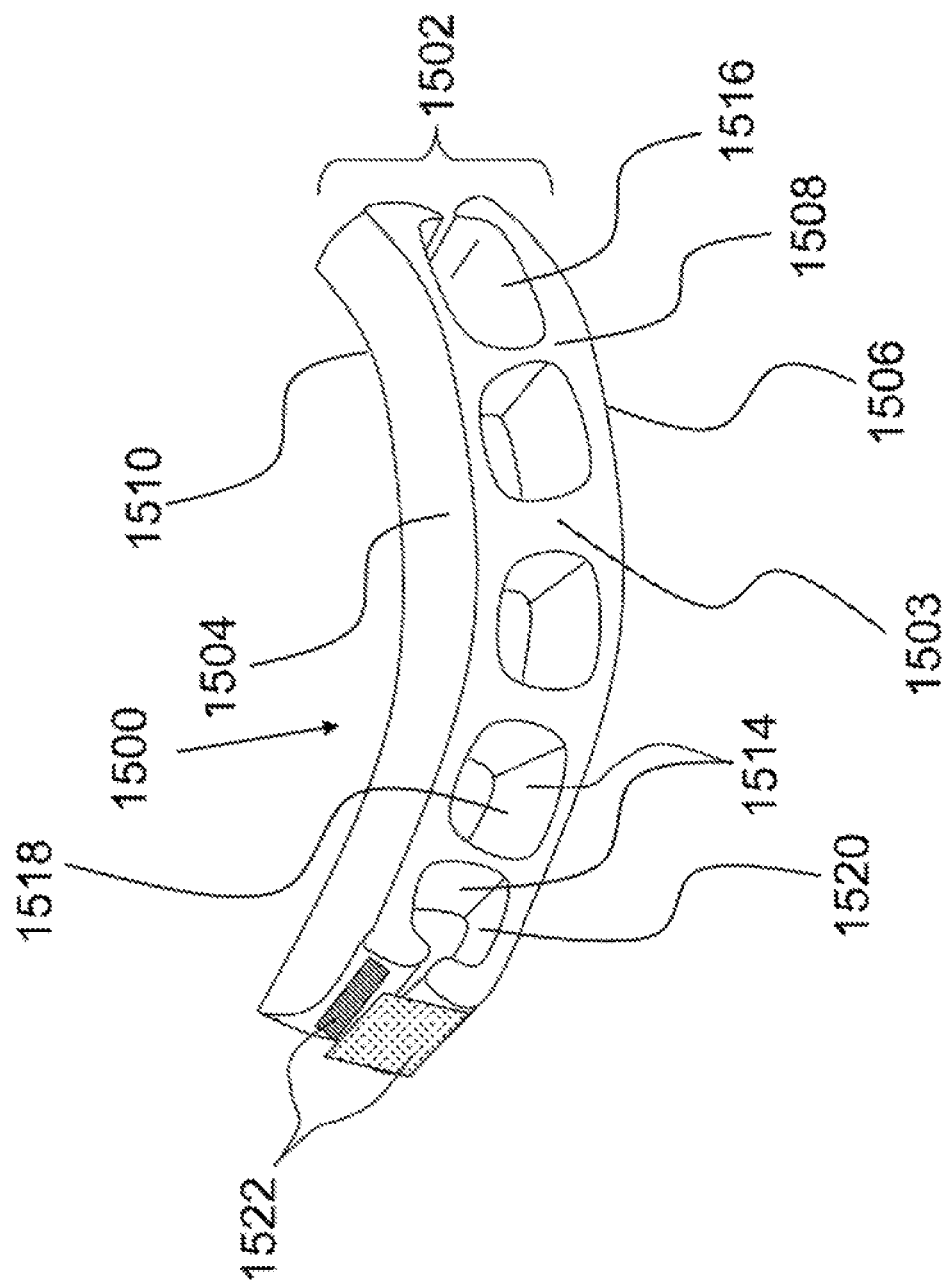
FIG. 15 is an illustration of a foot-therapy and toe-aligning device according to the present invention.

Another aspect of a foot-therapy and toe-aligning device 1500 according to the present invention is shown in FIG. 15. The foot-therapy and toe-aligning device 1500 comprises a frame 1502 with a separator 1503 for separating a plurality of toes. The frame 1502 may be constructed of any suitable material, non-limiting examples of which include plastic, silicone, and cork. Additionally, the frame 1502 may be optionally inflatable or filled with a fluid. When inflatable, the frame 1502 may be inflatable to various pressures. Furthermore, the frame 1502 may be formed through any suitable means for forming a frame 1502, non-limiting examples of which include injection molding, cast molding, compression molding, and extrusion molding. The frame 1502 has a top portion 1504, a bottom portion 1506, a front portion 1508, and a back portion 1510.

Included in the frame 1502 are a plurality of holes 1514, each configured for insertion of a toe. Each hole has an entrance on the back portion 1510, an exit on the front portion 1508, and surrounding walls 1516. The surrounding walls 1516 may be flat, curved or any other suitable shape to accommodate a toe. Additionally, the surrounding walls 1516 in at least one hole of the plurality of holes 1514 is continuous and thereby sealed, serving as a sealed toe hole 1518. Additionally, the surrounding walls 1516 in at least one other hole in the plurality of holes 1514 is non-continuous and thereby not sealed, serving as an openable toe hole 1520 allowing for easy insertion of a corresponding toe or toes.

The openable toe hole 1520 may be sealed through use of an enclosure 1522. Furthermore, the enclosure 1522 may be any suitable device or mechanism for attaching one medium with another, non-limiting examples of which include Velcro, snaps, an elastic band, hole and pin, and a male/female joint system.

Figure 16:
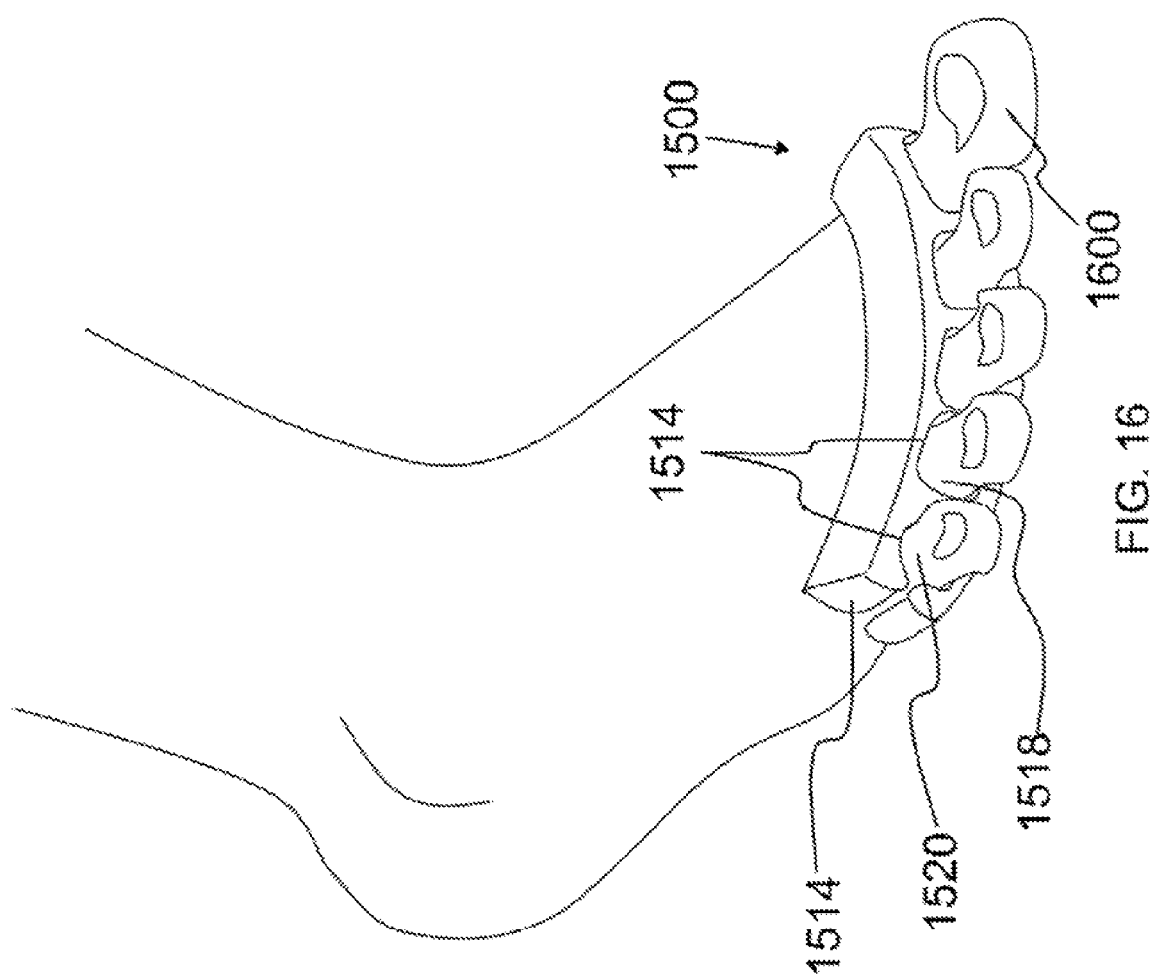
FIG. 16 is an illustration of a foot-therapy and toe-aligning device according to the present invention, with toes inserted therein.

A foot-therapy and toe-aligning device 1500 with toes 1600 inserted therein, is illustrated in FIG. 16. Although at least one hole in the plurality of holes 1514 serves as a sealed toe hole 1518, at least one other hole in the plurality of holes 1514 is not sealed and serves as an openable toe hole 1520. Because the openable toe hole 1520 is not sealed, the foot-therapy and toe-aligning device 1500 may be easily distorted and manipulated to allow easy insertion as well as articulation and accommodation of toes 1600 therein. The significance of the openable toe hole 1520 is that without the openable toe hole 1520, the toe stretcher is not easily manipulated, thereby making it difficult to utilize existing toe stretchers.

The foot-therapy, exercise, and toe aligning device 1500 teaches specific combinations of one or more closed and openable toe holes that provides for a superior balance of convenience for placing and securing the device on the toes. These specific combinations also provide for superior therapeutic and exercise benefits for people with variations in foot and toe structure, foot conditioning, and pathology. The size, shape, and location of the toe hole openings provides unique and unanticipated benefits for people with varying foot and toe structures, conditions and pathology.

There are unique and novel advantages in the accommodation of toe movement/articulation, in passive and active use of the device 1500 that result from combinations of openable and closed toe openings. For example, a completely closed toe opening limits the amount of freedom (articulation) of movement that is available to the toes and feet. Under many circumstances, such as stiff toes and pathologic foot conditions (i.e., bunions, hammer toes, cross toes, etc.), a specific combination of closed and openable toe hole openings yields a more convenient and superior exercise and therapeutic result.

It should be noted that the configuration of the foot-therapy and toe-aligning device 1500 illustrated in FIGS. 15 through 19 can include each of the devices and elements that are attached to or within the frame (and posts) as described and illustrated in FIGS. 1 through 14. For example and as can be appreciated by one skilled in the art, the reservoir, electronic devices, processing units, etc., can also be attached with (or within, as applicable) the frame 1502 of FIG. 15 to provide an equivalent function to the user. It should also be noted that the mechanisms, elements, and devices described and illustrated with respect to FIGS. 17 through 19 can also be attached with and used with the foot-therapy and toe-aligning device 100 that is illustrated in FIGS. 1 through 14.

As shown in FIG. 17, the foot-therapy and toe-aligning device 1500 can also include a variety of implantation elements. In addition to the electronic devices described above, the implantation element is any suitable element that can be implanted, either fully or partially, within the foot-therapy and toe-aligning device 1500. Although illustrated as being fully implanted at various locations within the foot-therapy and toe-aligning device 1500, the present invention is not intended to be limited thereto as the implantation elements, nor their implantation depths, can be affixed within the device 1500 at any desired location and at any desired implantation depth.

The implantation element can be used to provide a variety of cosmetic, ornamental, entertainment, therapeutic, and educational benefits. As a non-limiting example, the implantation element is a light or a series of lights 1700. The lights 1700 can be used for a variety of purposes, non-limiting examples of which include light therapy and messaging. For example, the lights 1700 can be used for light therapy, where the light being emitted is within a range of the light spectrum (e.g., infrared) that provides a therapeutic benefit to the user.

As another example, the lights 1700 can be used as a messaging system. If the lights are used as a light messaging system (such as a light emitting diode (LED) system), the lights 1700 can be used to generate a variety of messages for entertainment, educational, ornamental, and advertisement purposes. In another aspect, the implantation element can be a display device 1702 that is used to display a variety of messages. As a non-limiting example, the display device 1702 can be a plastic disk (or any other suitable shape) that includes logos of recognizable sports teams, groups, companies, events, etc. (e.g., Coca-Cola™, Detroit Red Wings™, Beverly Hills Hotel™, etc.). As described above, the foot-therapy and toe-aligning device 1500 can be formed of a transparent material (e.g., a clear or colorless elastomeric gel or other transparent material). It should be noted that the device 1500 can also be formed of translucent tents with color that allow for light to pass therethrough. Thus, when the display device 1702 is inserted within the foot-therapy and toe-aligning device 1500, a user can easily see and read any messages imprinted upon or otherwise displayed by the display device 1702.

Another non-limiting example of an implantation element is a thermometer 1704 or other suitable sensing device. As described above, the thermometer 1704 (or other sensing device) can be used to monitor and control the biological functions of the user to provide for therapeutic benefits.

As yet another non-limiting example, the implantation element can be a magnet 1706 or several magnets. As can be appreciated by one skilled in the art, the magnet 1706 can be used to provide a therapeutic benefit to the user. In another aspect, the magnet 1706 can be used to attach an external object with the device 1500 and thereby operate as an attachment mechanism.

Figure 18:
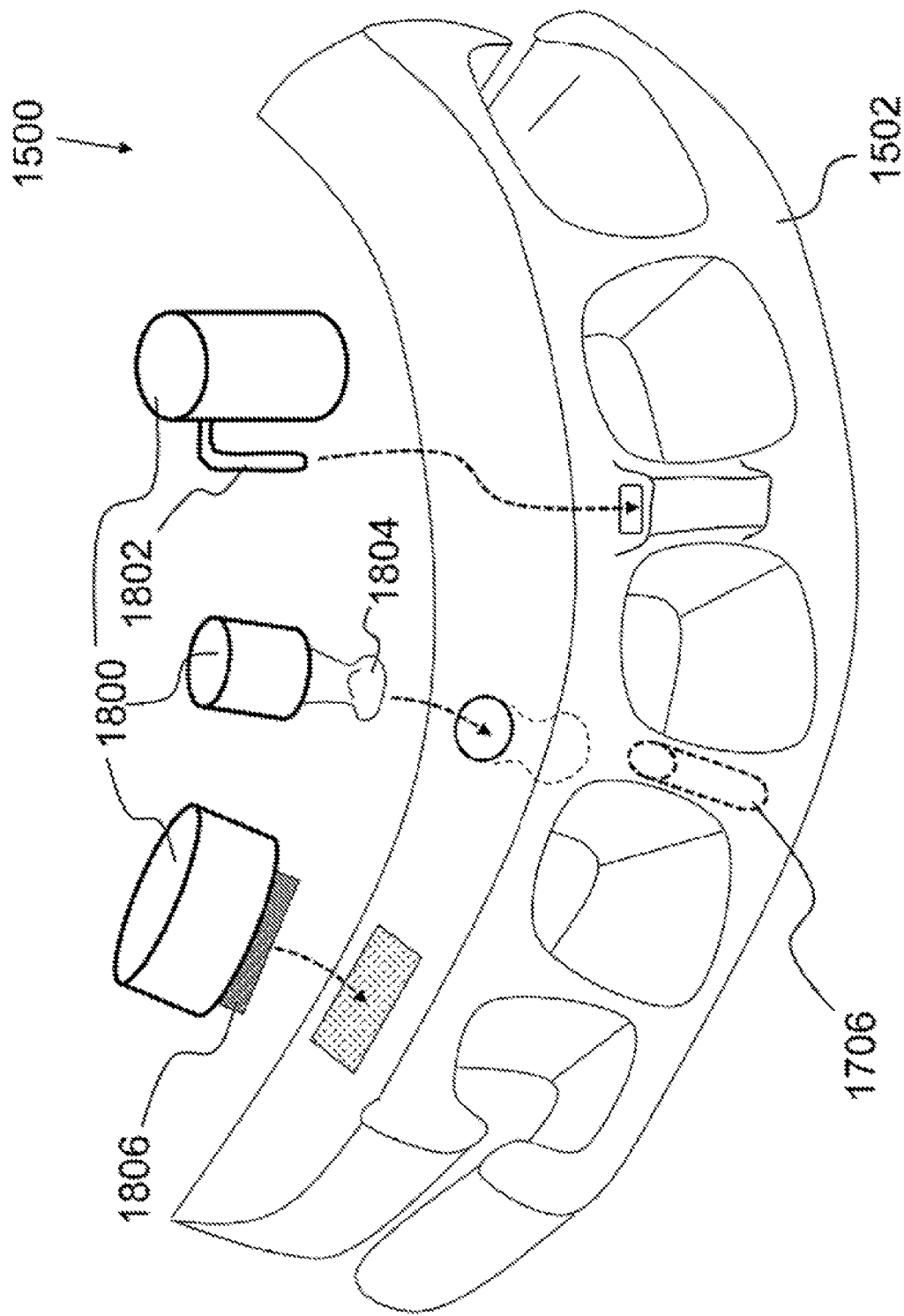
FIG. 18 is an illustration of a foot-therapy and toe-aligning device according to the present invention, illustrating external objects being attached with the device via an attachment mechanism.

As shown in FIG. 18, the present invention also includes an attachment mechanism that is attached with the frame 1502. The attachment mechanism is any suitable mechanism or device that is operable for detachably attaching an external object 1800 with the device 1500. Non-limiting examples of such attachment mechanisms include a magnet 1706 system, a clip mechanism 1802, a male/female plug mechanism 1804, and a hook and loop fastener (e.g. Velcro) 1806. The external object 1800 is any suitable object that is desirable for connecting with the device 1500. For example, each of the electronic devices and implantation elements as described above can be attached with the device 1500 as an external object 1800. As yet a further example, the display device (illustrated as element 1702 in FIG. 17) can be affixed externally as an external object 1800 instead of being implanted within the device 1502.

Figure 19:
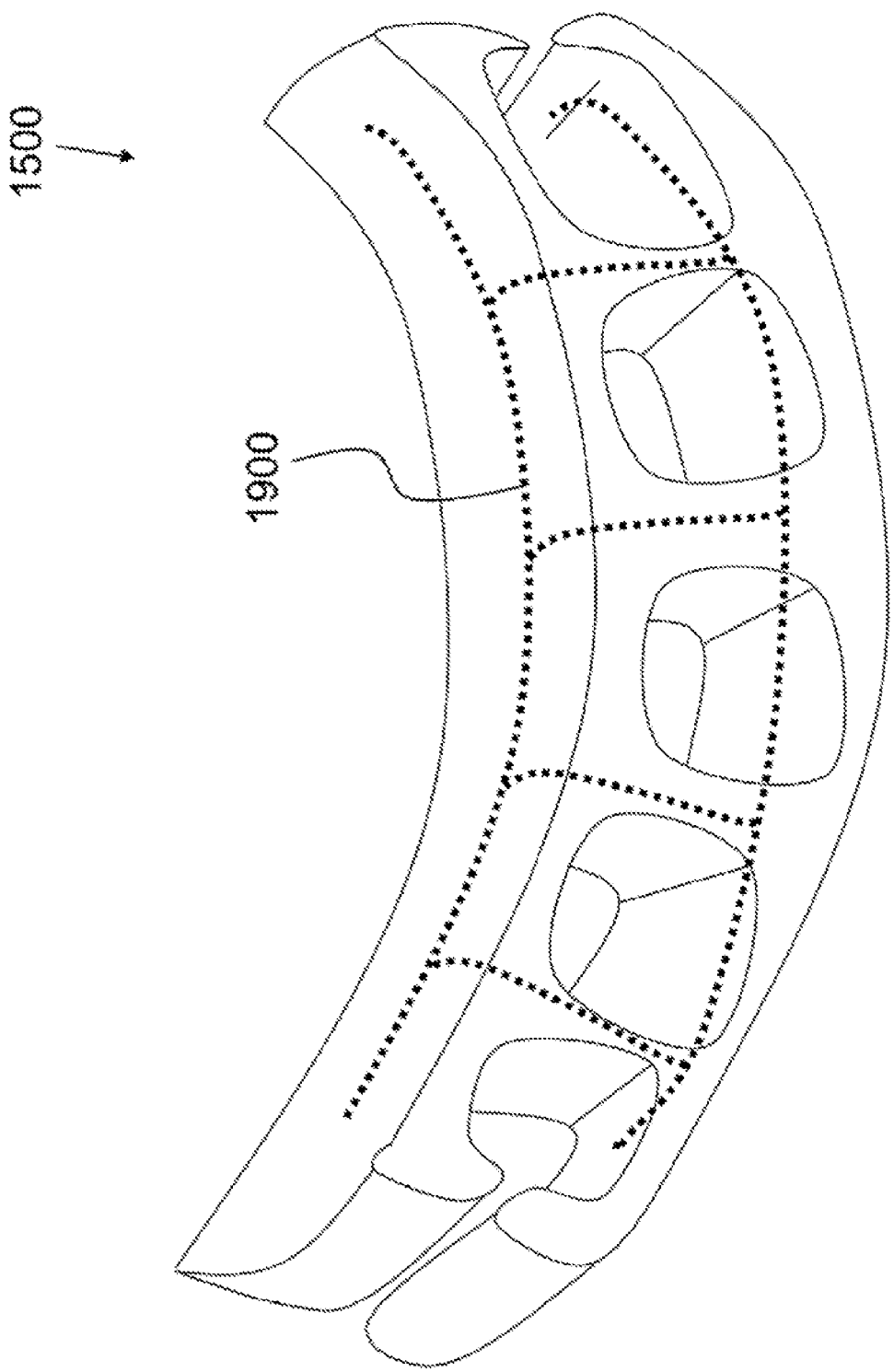
FIG. 19 is an illustration of a foot-therapy and toe-aligning device according to the present invention, illustrating a support structure.

As described above with respect to FIG. 14, the present invention also includes a support structure 1400, either preformed or formable. Although FIG. 14 illustrates the support structure 1400 as being inserted within only the toe posts 112, the present invention is not intended to be limited thereto. As shown in FIG. 19, the support structure 1900 can be formed throughout (and within) the device 1500 to allow a user to customize the shape of the device 1500. In this aspect, the support structure 1900 is malleable or bendable such that it operates as a formable armature. The support structure 1900 is formed of any suitably re-shapeable material that maintains a new shape once positioned in the new shape, a non-limiting example of which includes metallic wire. Thus, using the support structure 1900, a user can alter the shape of the device 1500 to increase comfort, etc.

In summary, the present invention is an exercise foot-therapy and toe-aligning device that is formed to include a myriad of features. Examples of such features include educational benefits, therapeutic effects, advertisement opportunities, etc. Such features are provided using a variety of devices and implementations (e.g., implantation elements, electronic devices, external objects, reservoir, support structure, etc.) that can be used with each of the aspects illustrated in FIGS. 1 through 19.

What is claimed is:
1. A foot-therapy and toe-aligning device, comprising:
a frame having a top portion and a bottom portion, each of which extends lengthwise along a frame length between spaced apart first and second ends of the frame, and further comprising a front portion having a front edge, and a back portion having a back edge;

four separators integrally formed with and extending between the top and bottom portions of the frame to define at least three sealed toe holes arranged side-by-side along the frame length between adjacent separators when the separators are in a rest position, each of the four separators having a length extending between the top portion and the bottom portion of the frame and, further, each of the separators being formed of an elastic material having elastomeric properties that permit the separators to stretch and elongate along their lengths when the top and bottom portions of the frame are pulled apart and, thereafter, to relax and contract along their lengths and return to their rest position when the pulling apart of the top and bottom portions of the frame subsides, each of the sealed toe holes having an entrance at the back portion of the frame, an exit at the front portion of the frame, and a continuous surrounding wall that circumscribes the toe hole, the continuous side wall of each sealed toe hole being an integrally formed, continuous, and unbroken surrounding wall formed by the adjacent separators and corresponding top and bottom portions of the frame, wherein the sealed toe holes extend between the front and back portions of the frame and are arranged along the frame length and configured to receive toes of a human foot when the separators are in their rest position; and wherein an electronic device is connected with at least one of the frame and a separator.

2. A method of using a foot-therapy and toe-aligning device, the method comprising:

providing a foot-therapy and toe-aligning device comprising a frame with a frame length, the frame having a top portion and a bottom portion that extend lengthwise along the frame length between spaced apart first and second ends of the frame and further comprising a front portion having a front edge and a back portion having a back edge, the foot-therapy and toe-aligning device further comprising four solid separators formed of an elastic material having elastomeric properties that are spaced apart along the frame length and integrally formed with the top portion and bottom portion of the frame such that the separators connect the top portion and the bottom portion, the solid separators in combination with the top portion and the bottom portion of the frame forming at least three sealed and continuous toe holes arranged side-by-side along the frame length for insertion of at least three toes, each of the at least three toe holes including an entrance into a back portion of the frame, an exit from a front portion of the frame, and an integrally formed, continuous and unbroken surrounding wall, wherein at least one of the frame and the separators are formed such that an electronic device is connected with at least one of the frame and a separator;

stretching the foot-therapy and toe-aligning device from a rest position before insertion of at least three toes into the device, wherein stretching the device includes pulling the top and bottom portions of the frame apart to cause each of the four solid separators to elongate along a toe post length, which extends between the top and bottom portions of the frame, and to become thinner in cross section so that the at least three toe holes become distorted;

inserting the at least three toes into the foot-therapy and toe-aligning device while the device is stretched, wherein inserting the at least three toes into the device includes placing the at least three toes into the at least three toe holes while the toe holes are distorted, with each toe hole accommodating one toe; and releasing the foot-therapy and toe-aligning device after insertion of the at least three toes into the device, wherein releasing the device causes each of the four solid separators to contract along its toe post length such that the at least three toe holes to conform to the inserted toes.

* * * * *